(12) United States Patent
Liang et al.

(10) Patent No.: US 11,100,685 B2
(45) Date of Patent: Aug. 24, 2021

(54) METHOD AND APPARATUS FOR DETECTION AND VISUALIZATION OF PULMONARY EMBOLISM

(71) Applicant: Arizona Board of Regents on Behalf of Arizona State University, Scottsdale, AZ (US)

(72) Inventors: Jianming Liang, Scottsdale, AZ (US); Nima Tajbakhsh, Los Angeles, CA (US); Jaeyul Shin, Chandler, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 16/556,135

(22) Filed: Aug. 29, 2019

(65) Prior Publication Data

US 2020/0074701 A1 Mar. 5, 2020

Related U.S. Application Data

(60) Provisional application No. 62/724,092, filed on Aug. 29, 2018.

(51) Int. Cl.
*G06T 11/00* (2006.01)
*G06T 19/20* (2011.01)
(Continued)

(52) U.S. Cl.
CPC ............ *G06T 11/008* (2013.01); *G06T 19/20* (2013.01); *G16H 30/20* (2018.01); *G16H 30/40* (2018.01);
(Continued)

(58) Field of Classification Search
CPC ..... G06T 7/0012; G06T 11/008; G06T 19/20; G06T 2210/41; G06T 2219/028;
(Continued)

(56) References Cited

U.S. PATENT DOCUMENTS 9,152,926 B2 10/2015 Liang et al.
9,603,554 B2 3/2017 Liang et al.
(Continued)

FOREIGN PATENT DOCUMENTS

WO 2012109670 A1 8/2012
WO 2012109676 A1 8/2012
(Continued)

OTHER PUBLICATIONS

Roth et al., "Improving Computer-Aided Detection Using Convolutional Neural Networks and Random View Aggregation", IEE Transactions on Medical Imaging, vol. 35, No. 5, May 2016 (Year: 2016).*
(Continued)

*Primary Examiner* — Diane M Wills
(74) *Attorney, Agent, or Firm* — Elliot, Ostrander & Preston, P.C.

(57) ABSTRACT

Detecting a pulmonary embolism (PE) in an image dataset of a blood vessel involves obtaining a volume of interest (VOI) in the blood vessel, generating a plurality of PE candidates within the VOI, generating a set of voxels for each PE candidate, estimating for each PE candidate an orientation of the blood vessel that contains the PE candidate, given the set of voxels for the PE candidate, and generating a visualization of the blood vessel that contains the PE candidate using the estimated orientation of the blood vessel that contains the PE candidate.

14 Claims, 20 Drawing Sheets

(51) Int. Cl.
- G16H 30/20 (2018.01)
- G16H 50/20 (2018.01)
- G16H 30/40 (2018.01)
- A61B 8/08 (2006.01)
- A61B 5/026 (2006.01)
- A61B 6/00 (2006.01)

(52) U.S. Cl.
CPC ............ *G16H 50/20* (2018.01); *A61B 5/0263* (2013.01); *A61B 6/5217* (2013.01); *A61B 8/5223* (2013.01); *G06T 2210/41* (2013.01); *G06T 2211/404* (2013.01); *G06T 2219/028* (2013.01); *G06T 2219/2004* (2013.01)

(58) Field of Classification Search
CPC ...... G06T 2219/2004; G06T 2211/404; G16H 30/20; G16H 50/20; G16H 50/30; G16H 30/40; A61B 5/0263; A61B 6/5217; A61B 8/5223; A61B 6/504; A61B 8/0891; A61B 6/032

See application file for complete search history.

(56) References Cited

U.S. PATENT DOCUMENTS

| | | | |
|---|---|---|---|
| 9,684,957 | B2 | 6/2017 | Wu et al. |
| 9,700,213 | B2 | 7/2017 | Tajbakhsh et al. |
| 9,741,116 | B2 | 8/2017 | Liang et al. |
| 9,747,687 | B2 | 8/2017 | Tajbakhsh et al. |
| 9,924,927 | B2 | 3/2018 | Shin et al. |
| 9,959,615 | B2 | 5/2018 | Liang et al. |
| 9,978,142 | B2 | 5/2018 | Chi et al. |
| 10,052,027 | B2 | 8/2018 | Tajbakhsh et al. |
| 10,055,843 | B2 | 8/2018 | Tajbakhsh et al. |
| 10,120,980 | B2 | 11/2018 | Liang |
| 10,157,467 | B2 | 12/2018 | Dincer et al. |
| 10,610,203 | B2 | 4/2020 | Liang et al. |
| 2008/0125648 | A1* | 5/2008 | Bi ................ G06T 7/0012 600/425 |
| 2014/0072191 | A1 | 3/2014 | Liang |
| 2017/0004619 | A1* | 1/2017 | Liang ............ A61B 6/032 |
| 2017/0039711 | A1* | 2/2017 | Dincer ............ G06T 7/136 |
| 2017/0124701 | A1 | 5/2017 | Liang et al. |
| 2018/0225820 | A1 | 8/2018 | Liang et al. |
| 2018/0314943 | A1 | 11/2018 | Liang et al. |
| 2019/0332896 | A1 | 10/2019 | Liang et al. |
| 2020/0074271 | A1 | 3/2020 | Liang et al. |

FOREIGN PATENT DOCUMENTS

| | | |
|---|---|---|
| WO | 2013116865 A1 | 8/2013 |
| WO | 2013116867 A1 | 8/2013 |
| WO | 2015031641 A1 | 3/2015 |
| WO | 2015113014 A1 | 7/2015 |
| WO | 2015142808 A1 | 9/2015 |
| WO | 2015164724 A1 | 10/2015 |
| WO | 2015164768 A1 | 10/2015 |
| WO | 2016161115 A1 | 10/2016 |
| WO | 2017027475 A1 | 2/2017 |

OTHER PUBLICATIONS

Al-Hinnawi, et al., "Collaboration between interactive three-dimensional visualization and computer aided detection of pulmonary embolism on computed tomography pulmonary angiography views" (2018), Radiological Physics and Technology 11, pp. 61-72, https://doi.org/10.1007/s12194-017-0438-x,doi:10.1007/s12194-017-0438-x.

Bouma, H., et al., "Automatic detection of pulmonary embolism in cta images," Medical Imaging (2009), pp. 1223-1230.

Buhmann, S., et al., "Clinical evaluation of a computer-aided diagnosis (cad) prototype for the detection of pulmonary embolism," Academic Radiology (2007), pp. 651-658.

Calder, K., et al., "The mortality of untreated pulmonary embolism in emergency department patients," Annals of emergency medicine (2005), pp. 302-310.

Ciresan, D., et al., "Multi-column deep neural networks for image classification," Computer Vision and Pattern Recognition (CVPR), 2012 IEEE Conference (2012), pp. 3642-3649.

Ding, et al., "Accurate pulmonary nodule detection in computed tomography images using deep convolutional neural networks, in: International Conference on Medical Image Computing and Computer-Assisted Intervention," (2017) Springer, pp. 559-567.

Engelke C., et al. "Computer-assisted detection of pulmonary embolism: performance evaluation in consensus with experienced and inexperienced chest radiologists," European radiology (2008), pp. 298-307.

Fairfield, J., "Toboggan contract enhancement for contrast segmentation," Pattern Recognition, 1990. Proceedings., 10th International Conference on vol. 1, IEEE (1990), pp. 712-716.

Glorot, X., et al., "Understanding the difficulty of training deep feed forward neural networks," International conference on artificial intelligence and statistics (2010), pp. 249-256.

He, K., et al., "Deep residual learning for image recognition," Proceedings of the IEEE conference on computer vision and pattern recognition (2016), pp. 770-778.

Huang, G., et al., "Densely connected convolutional networks," Proceedings of the IEEE conference on computer vision and pattern recognition, vol. 1 (2017), p. 3.

Jia, Y., et al., "Convolutional architecture for fast feature embedding," arXiv preprint arXiv:1408.5093 (2014), 4 pages.

Krizhevsky, A., et al., "Imagenet classification with deep convolutional neural networks," Advances in neural information processing systems (2012), pp. 1097-1105.

Lecun, Y., et al., "Backpropagation applied to handwritten zip code recognition," Neural computation 1 (1989), pp. 541-551.

Liang, J., et al., "Computer aided detection of pulmonary embolism with tobogganing and multiple instance alassification in CT pulmonary angiography," Information Processing in Medical Imaging (2007), pp. 630-641.

Maizlin, Z.V., et al., "Computer-aided detection of pulmonary embolism on ct angiography: initial experience," Journal of Thoracic Imaging (2007), pp. 324-329.

Masoudi, et al., "A new dataset of computed-tomography angiography images for computer-aided detection of pulmonary embolism, in: Scientificdata" (2018), 9 pages.

Ozkan, H., et al., "A novel method for pulmonary embolism detection in cta images," Computer methods and programs in biomedicine 113 (3) (2014), pp. 757-766.

Park. S.C., et al., "A multistage approach to improve performance of computer-aided detection of pulmonary embolisms depicted on CT images," Preliminary investigation, Biomedical Engineering, IEEE Transactions on 58 (6) (2011), pp. 1519-1527.

Prasoon, A., et al., "Deep feature learning for knee cartilage segmentation using a triplanar convolutional neural network," Medical Image Computing and Computer-Assisted Intervention-MICCAI (2013), pp. 246-253.

Roth, H., et al., "A new 2.5d representation for lymph node detection using random sets of deep convolutional neural network observations," Medical Image Computing and Computer-Assisted Intervention MICCAI, vol. 8673 of Lecture Notes in Computer Science (2014), pp. 520-527.

Roth, H., et al., "Detection of sclerotic spine metastases via random aggregation of deep convolutional neural network classifications," Recent Advances in Computational Methods and Clinical Applications for Spine Imaging, vol. 20 of Lecture Notes in Computational Vision and Biomechanics (2015), pp. 3-12.

Roth, H.R., er al., "Deep convolutional networks for pancreas segmentation in ct imaging," SPIE Medical Imaging, International Society for Optics and Photonics (2015), 8 pages.

Roth, H.R., et al., "Improving computer-aided detection using convolutional neural networks and random view aggregation," IEEE Transaction in Medical Imaging (2016), 12 pages.

Sadigh, G., et al., "The morality of untreated pulmonary embolism imaging" (2011), American Journal of Roentgenology 196(3), pp. 497-515.

(56) References Cited

OTHER PUBLICATIONS

Setio, A. A. A., et al., "Pulmonary nodule detection in ct images: false positive reduction using multi-view convolutional networks," IEEE transactions on medical imaging 35 (2016), pp. 1160-1169.
Simonyan, K., et al., "Very deep convolutional networks for large scale image recognition" (2014), arXiv preprint arXiv:1409.1556, 13 pages.
Szegedy, C., et al., "Going deeper with convolutions," Proceedings of the IEEE Conference on Computer Vision and Pattern Recognition (2015), pp. 1-9.
Tajbakhsh, N., et al., "A comprehensive computer-aided polyp detection system for colonoscopy videos," Information Processing in Medical Imaging (2015), pp. 327-338.
Tajbakhsh, N., et al., "Computer-aided pulmonary embolism detection using a novel vessel-aligned multi-planar image representation and convolutional neural networks," Medical Image Computing and Computer-Assisted Intervention (2015), 8 pages.
Tajbakhsh, N., et al., "Convolutional neural networks for medical image analysis: Full training or tine tuning?" IEEE transactions on medical imaging (2016), pp. 1299-1312.
Tajbakhsh, N., et all., "Automated polyp detection in colonoscopy videos using shape and context information," Medical Imaging, IEEE Transactions (2016), pp. 630-644.
Tajbaksh, N., et al., "Automatic polyp detection in colonoscopy videos using an emsemble of convolutional neural networks, in: Biomedical Imaging (ISBI)," 2015 IEEE 12th International Symposium on, IEEE (2015), pp. 79-83.
U.S. Appl. No. 16/875,680, filed May 15, 2020, Siddiquee, et al.
U.S. Appl. No. 16/885,579, filed May 28, 2020, Zhou, et al.
Wang, X., et al., "Improving performance of computer-aided detection of pulmonary embolisms by incorporating a new pulmonary vascular-tree segmentation algorithm," SPIE Medical Imaging, International Society for Optics and Photonics (2012), pp. 83152U1-83152U8.
Zhou, C., et al., "Preliminary investigation of computer-aided detection of pulmonary embolism in three-dimensional computed tomography pulmonary angiography images 1," Academic Radiology 12 (2005), pp. 782-792.
Zhou et al., "Fine-tuning convolutional neural networks for biomedical image analysis: Actively and incrementally" (2017), The IEEE Conference on Computer Vision andPattern Recognition (CVPR), pp. 4761-4772.
Zhu, et al., "Deepem: Deep 3d convnets 80 with em for weakly supervised pulmonary nodule detection, in: International Conference on Medical Image Computing and Computer-Assisted Intervention" (2018), Springer, pp. 812-820.

\* cited by examiner

METHOD AND APPARATUS FOR DETECTION AND VISUALIZATION OF PULMONARY EMBOLISM

CROSS-REFERENCE TO RELATED APPLICATIONS

This application claims priority to U.S. provisional patent application No. 62/724,092, filed Aug. 29, 2018, the entire contents of which are incorporated herein by reference.

STATEMENT REGARDING FEDERALLY SPONSORED RESEARCH

This invention was funded by a government agency. This invention was made with government support under R01 HL128785 awarded by the National Institutes of Health. The government has certain rights in the invention.

TECHNICAL FIELD

Embodiments of the invention relate to medical imaging. In particular, embodiments of the invention relate to detecting a pulmonary embolism in an image dataset.

BACKGROUND

Pulmonary embolism (PE) is a "blood clot" that travels from the legs, or less commonly other parts of the body, to the lungs where it blocks central, lobar, segmental, or subsegmental pulmonary vessels depending on its size. PE, if left undiagnosed, leads to a mortality rate that may approach 30% in emergency department patients. However, with early diagnosis and treatment, the mortality rate decreases to as low as 2%. A primary imaging technique for PE diagnosis is computed tomography pulmonary angiography (CTPA), in which a PE appears as a filling defect (essentially, the PE appears as a darker area) in the bright lumen of a pulmonary artery. With reference to FIGS. 1A and 1B, an embolus appears as a darker filling defect surrounded by a brighter, contrast-enhanced, vessel lumen. In particular, FIG. 1A depicts an embolus causing a mild degree of obstruction in a segmental artery, represented by a relatively smaller darker area 115 within the bright lumen of the pulmonary artery, whereas FIG. 1B depicts a large embolus in a segmental artery, represented by a relatively larger darker area 120 within the lumen of the pulmonary artery. The left, middle, and right views 100, 105, and 110, present the axial, sagittal, and coronal image planes of the same image, respectively.

PE diagnosis in CTPA images is not trivial. First, a PE can appear in central, segmental, or subsegmental arteries. Therefore, radiologists need to inspect the large network of pulmonary arteries through numerous CT slices in search of a filling defect. Second, a PE appears in various sizes and degrees of arterial occlusion, requiring radiologists to be very sensitive to the visual characteristics of a PE. Third, PE diagnosis can be compromised in the presence of other pulmonary diseases or when the quality of the CT image is degraded, because both factors can cause a large number of PE mimics in images, which need to be distinguished from the actual pulmonary emboli. Therefore, PE diagnosis can be a tedious, time-consuming, and error-prone task.

Computer-aided PE diagnosis has however proved effective in improving radiologists' diagnostic capabilities for PE assessment, but at the price of prolonged interpretation sessions. This is because current computer aided design and drafting (CAD) systems generate a relatively large number of false markings, which all have to be reviewed by radiologists. Another limitation of the current CAD systems is that they are not equipped with a rapid inspector by which radiologists can quickly review each CAD marking. Excessive time spent adjudicating CAD assessments creates a workflow that radiologists find unacceptable and may even impair the ultimate purpose of PE CAD, that of facilitating PE diagnosis.

Image representation coupled with Convolutional Neural Networks (CNNs) has been used to localize a PE in CTPA image datasets. It is understood that image representation can substantially influence the performance of CNNs for object detection and recognition. The choice of imaging representation is important when considering three-dimensional (3D) imaging applications. While the use of subvolumes (i.e., sets of image frames) may appear to be a natural image representation for a 3D imaging application, it incurs substantial computational cost and may also run the risk of over-fitting when limited labeled training data is available. Furthermore, storing 3D activation maps of deep 3D models in a graphics processor unit (GPU) memory is highly memory intensive. While it is possible to train and deploy such models over multiple GPUs, doing so requires expensive, computationally powerful machines, which certainly limits the applicability of such models in clinical practice. Finally, fine-tuning pre-trained two-dimensional (2D) CNNs has been shown to significantly improve the models trained for medical imaging applications. However, pre-trained 3D models are not yet as widespread as their 2D counterparts, and their quality may not be as competitive because the sizes of labeled medical imaging datasets are far smaller than, for example, the ImageNet database available at image-net.org. (ImageNet is an image database organized according to the WordNet (wordnet.princeton.edu) hierarchy in which each node of the hierarchy is depicted by hundreds and thousands of images). Therefore, it may be desirable to compress the 3D context into a 2D representation and then take advantage of the pre-trained 2D models.

The common approach to avoiding a high dimensional subvolume around an abnormality in image representations for 3D medical datasets is to form 3-channel patches using standard image planes (sagittal, coronal, and axial planes). However, this approach may not fully leverage the 3D information embedded in the 3D context. A multi-view approach has been suggested wherein the subvolume around an abnormality is interpolated in a number of predefined image planes. The drawback to this approach is that one needs to train a separate CNN model for each orientation of the interpolated image planes. Another approach has been suggested using a 2.5D image representation that can more effectively leverage information embedded in a subvolume. Such an image representation yields 3-channel patches where each channel is computed by interpolating the volume along two random spatial directions. More recently, a new context-aware image representation has been suggested that aligns itself with the blood vessel containing the abnormality, as opposed to the 2.5D approach which interpolates the volume along random directions independent of the context.

Thus, diagnosing pulmonary embolism (PE) and excluding disorders that may clinically and radiologically simulate PE poses a challenging task to both human and machine perception. What is needed is a novel vessel-oriented image representation (VOIR) according to embodiments of the invention that can improve the human and/or machine perception of PE through a consistent, compact, and discriminative image representation, and can also improve radiologists' diagnostic capabilities for PE assessment by serving as the backbone of an effective PE visualization system.

DETAILED DESCRIPTION

Embodiments of the invention provide an image representation of a blood vessel that can be used to train more effective convolutional neural networks for distinguishing PEs from PE mimics, and also allow radiologists to visually inspect the blood vessel lumen, from multiple perspectives, so that they can confidently report any filling defects in the image as PEs. Embodiments of the invention provide a novel, compact, and discriminative image representation of a blood vessel to reduce the large number of false alarms or PE mimics and improve the effectiveness of a PE visualization module. Specifically, embodiments of the invention involve a computer-aided PE diagnosis system which, in addition to detecting and generating an accurate set of PE markings, provides radiologists with an effective visualization tool so they can conveniently examine the blood vessel lumen from multiple perspectives and report filling defects, if any, with confidence.

Figure 7:
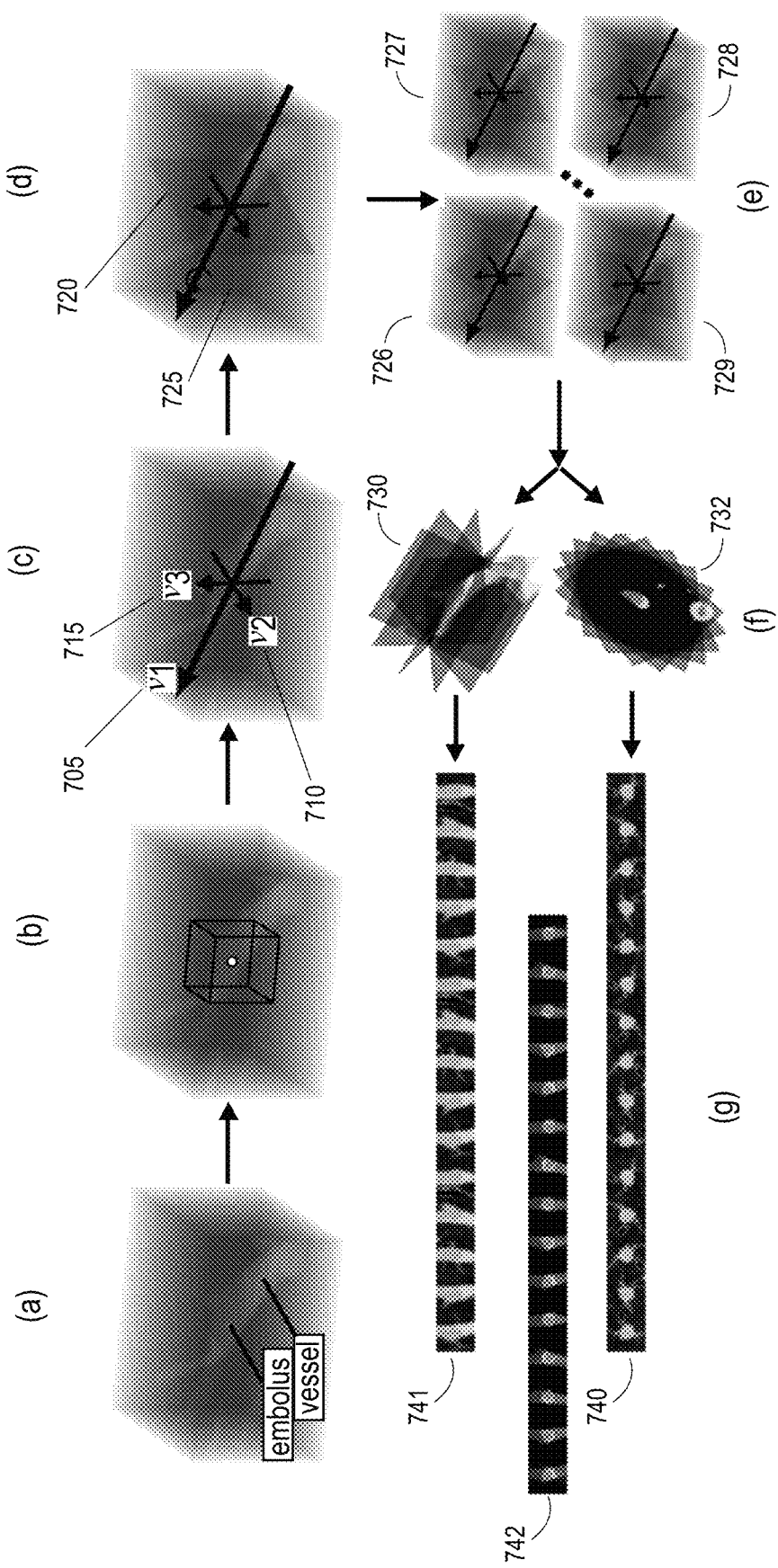
FIG. 7 provides an overview of a context-aware image representation according to an embodiment of the invention.

Embodiments of the invention provide a vessel-oriented image representation (VOIR). The image representation provided by embodiments of the invention has four properties that offer advantages:

(1) efficiency and compactness—concisely summarizing three-dimensional (3D) contextual information around an embolus in only three image channels. VOIR is compact because it concisely summarizes the 3D contextual information around emboli in only three image channels. As discussed before, a 3D image representation, although a seemingly obvious choice, can result in several complications: 1) it incurs substantially higher computational cost (3D convolution vs. 2D convolution), 2) it runs a higher risk of over-fitting due to a higher dimensional feature space, 3) it requires shallower architectures due to the high storage requirement for the 3D activation maps, and 4) it slows down the neural network training due to the inability to utilize high quality 2D models pre-trained using ImageNet. Therefore, a compact image representation is highly advantageous. With reference to FIG. 7, an overview of the context-aware image representation process in accordance with an embodiment of the invention 700 is provided. At (a), a subvolume is selected around an embolus. At (b), a small volume of interest (VOI) is centered on the candidate (the white dot). At (c), a principle component analysis (PCA) is performed in the VOI to determine the vessel axis $v_1$ 705 and the two orthogonal directions, $v_2$ 710 and $v_3$ 715. At (d), a cross-sectional image plane 720 and longitudinal image plane 725 are formed using $v_1$ 705, $v_2$ 710, and $v_3$ 715. At (e), by rotating $v_2$ 710 and $v_3$ 715 around $v_1$ 705, a number of cross sectional and longitudinal image planes 726, 727, 728, and 729, are obtained. At (f), the rotated image planes can be grouped in two envelopes—a longitudinal envelope 730 and a cross-sectional envelope 732. At (g), a 3-channel image representation for the embolus is generated by randomly selecting one image plane 740 from the cross-sectional envelope 732 and two image planes 741 and 742 from the longitudinal envelope 730.

Figure 8:
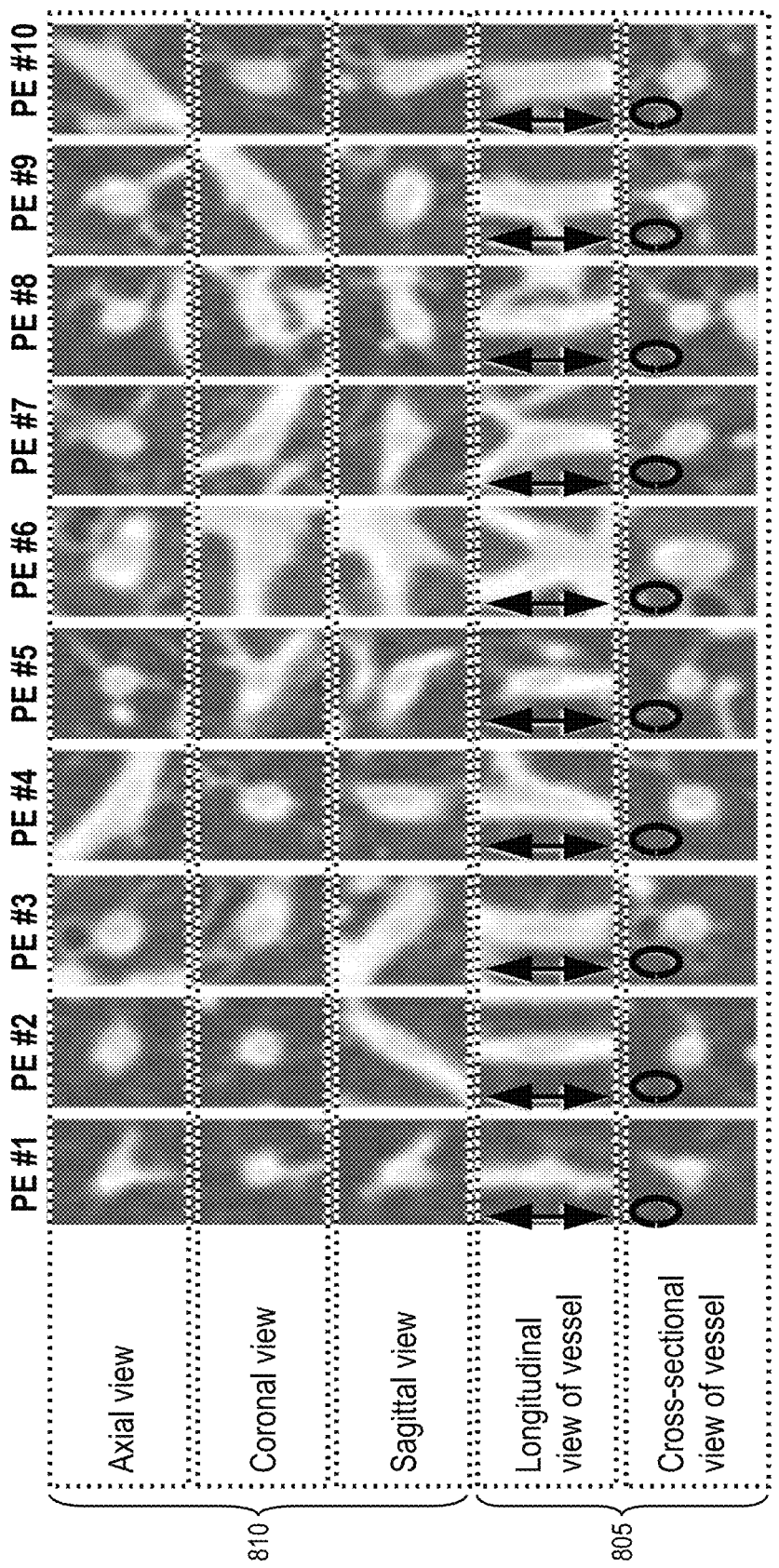
FIG. 8 is an image representation according to an embodiment of the invention that characterizes emboli consistently in the cross sectional and longitudinal image planes.

(2) consistency—automatically aligning the embolus in the three image channels according to the orientation of the affected vessel. VOIR is consistent with the orientation of the containing vessel. In general, emboli can affect pulmonary arteries in any orientation. As a result, images extracted from the axial, sagittal, coronal planes exhibit a significant amount of variation in the appearance of emboli. This in turn complicates the classification task and hinders effective utilization of CNNs. With the benefit of vessel alignment, VOIR allows for a standardized image representation whereby emboli consistently appear as elongated structures in the longitudinal vessel view and as circular structures in the cross-sectional vessel view. FIG. 8 illustrates at 800 variations in PE appearance using the image representation 805 according to embodiments of the invention, and a conventional image representation 810, based on sagittal, coronal and axial views.

Figure 9:
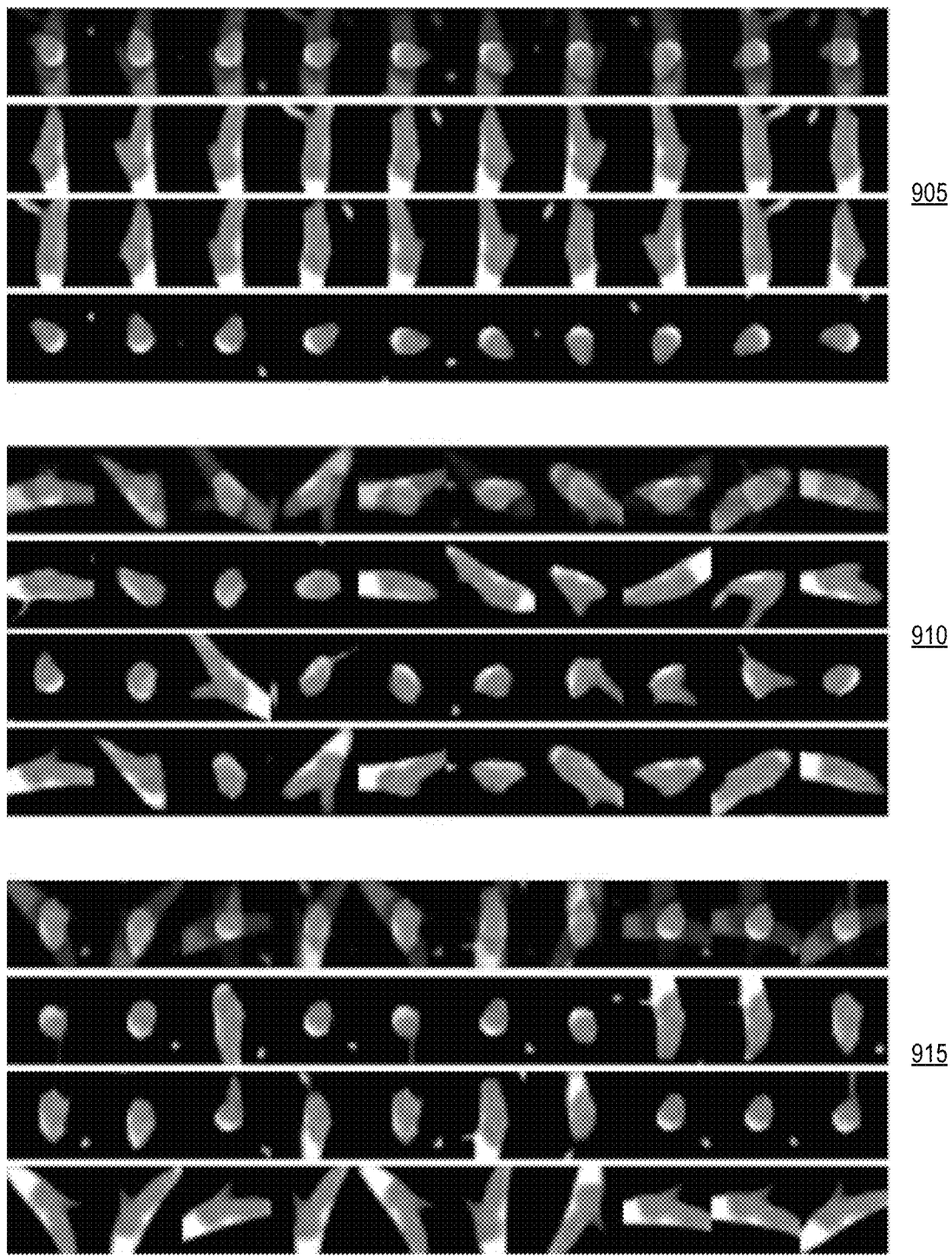
FIG. 9 illustrates a rotation-based data augmentation for an embolus according to an embodiment of the invention, a 2.5D approach, and a prior art—conventional—approach.

(3) expandability—naturally supporting data augmentation for training Convolutional Neural Networks (CNNs). Embodiments of the invention are expandable, supporting data augmentation, which is essential for effective training and testing of CNNs. In 2D applications, data augmentation is performed by applying arbitrary in-plane rotations and then collecting samples at multiple scales and translations. An image representation for 3D applications must also support the above operations to enable data augmentation. While it is straightforward to extend translation and scaling to a 3D space, the rotation operation can be problematic. Rotation around a random axis or around the standard x, y, z planes will not allow emboli to be displayed in a consistent, standardized fashion. With reference to FIG. 7, embodiments of the invention—VOIR—address this need by selecting images from the cross section envelope 732, which is equivalent to rotating the cross sectional plane 720 around the vessel axis $v_1$ 705. This is also the principle behind the 360 degree tour of a PE as described herein below. FIG. 9 illustrates consistency in appearance of a PE under rotation-based data augmentation, in accordance with embodiments of the invention. In particular, FIG. 9 illustrates rotation-based data augmentation for an embolus using an image representation (VOIR) according to an embodiment of the invention 905, according to a 2.5D approach 910, and using a conventional image representation 915 based on axial, sagittal, and coronal views. In each panel, the first row shows the resulting stacked channels and the second through fourth rows show the individual channels. While VOIR maintains a consistent PE appearance with rotation-based data augmentation, the 2.5D approach and the conventional image representations fail to provide a consistent appearance.

(4) multi-view visualization—maximally revealing or demonstrating intra-vascular filling defects. VOIR offers a multi-view representation of a PE, allowing radiologists to confirm or exclude the presence of emboli with confidence. The two animations generated using image representation according to embodiments of the invention, namely, axis alignment animation and a 360-degree tour animation, are also essential for rapid removal of false positive markings from any PE CAD system. False positives, if not visualized properly, can significantly prolong CTPA reading sessions, adversely affecting workflow and impairing adoption of CAD technology in clinical practice.

The first three properties and advantages described above are utilized in training an accurate false positive reduction model based on convolutional neural networks, while the fourth property is used in a PE visualization system according to embodiments of the invention. The capability of the PE visualization system for visualizing suspicious findings combined with the improved false positive reduction model makes embodiments of the invention more suitable for clinical practice.

According to embodiments of the invention, an embolus appears as a filling defect, which is essentially a darker spot or area, inside a bright, contrast-enhanced, pulmonary artery lumen. If a segment of the artery with an embolus is oriented obliquely to a standard image plane (axial, sagittal, or coronal), the embolus may not be seen clearly. Embodiments of the invention, therefor, reformat the image planes to substantially align them with the longitudinal axis of the vessel. An interpolation scheme guided by the vessel's longitudinal axis has the effect of maximally revealing the filling defects, thereby facilitating PE diagnosis for both radiologists and machines (i.e., CNNs). Indeed, vessel orientation estimation is used in both visualization and detection (diagnostic) systems according to embodiments of the invention. Estimating vessel orientation is discussed below, followed by a discussion of how vessel orientation is used in PE visualization and diagnosis, according to embodiments of the invention.

Estimating Orientation of a Blood Vessel

Figure 1A:
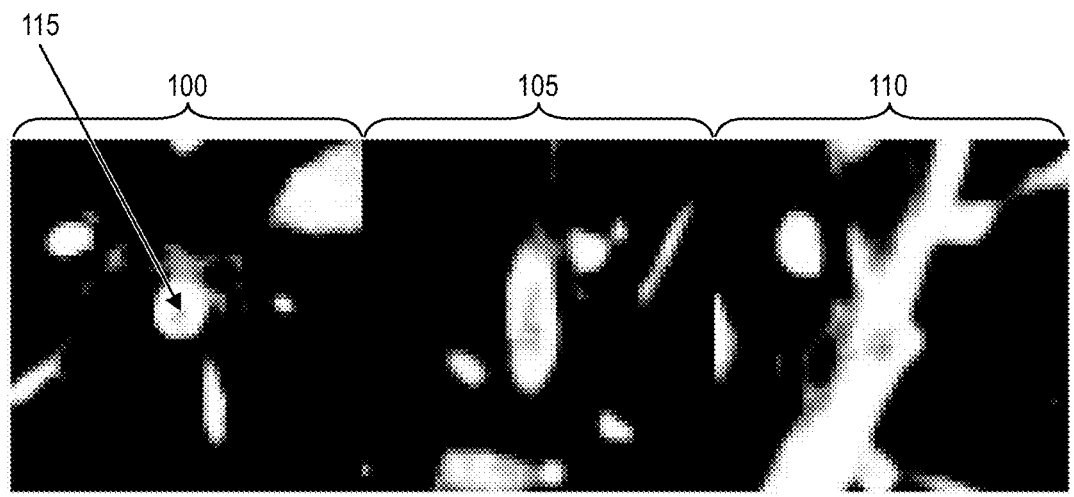
FIG. 1A is an image from a CTPA dataset of an embolus causing a mild degree of obstruction in a segmental artery, shown from the axial, sagittal, and coronal image planes.
Figure 1B:
FIG. 1B is an image from a CTPA dataset of a large embolus in a segmental artery, shown from the axial, sagittal, and coronal image planes.
Figure 2:
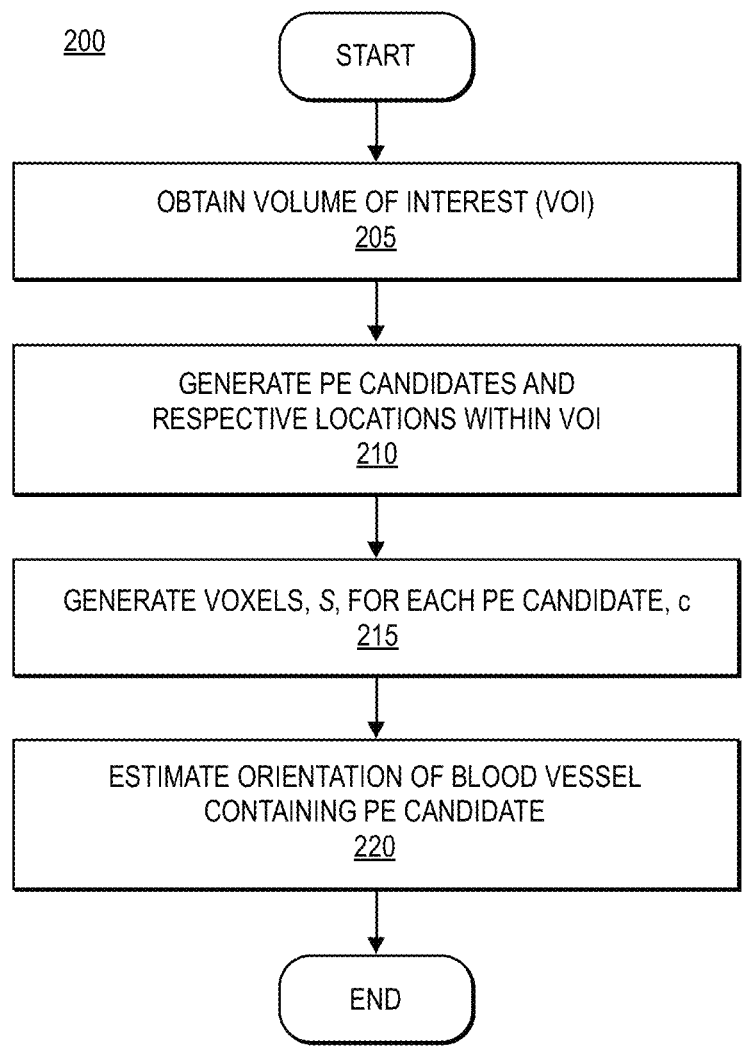
FIG. 2 is a flow chart for detecting a pulmonary embolism (PE) in accordance with an embodiment of the invention.

With reference to the flow chart in FIG. 2, a computer aided design and drafting (CAD) system for detecting a pulmonary embolism (PE) in a image dataset of a blood vessel in accordance with an embodiment of the invention 200 first involves logic 205 for extracting or obtaining one or more volumes of interest (VOI) of a lung or blood vessel depicted in the image dataset, such as a computed tomography pulmonary angiography (CTPA) image datatset. The VOI is a segment or region of the lung or blood vessel. It should be noted that while the primary imaging technique or type for PE detection/diagnosis is CTPA, in which a PE appears as a filling defect (i.e., a darker area) in a bright lumen of a pulmonary artery, the embodiments are generally applicable and not restricted to any particular imaging technique. For example, embodiments can be applied to detecting PEs and generating PE visualizations or visualizations of other pathologies in medical images obtained from various modalities (e.g., magnetic resonance imaging (MRI), ultrasound, etc.). Extracting a VOI of a lung or blood vessel typically involves dividing up the lung or blood vessel into two or more overlapping, or non-overlapping, segments, or regions, each identified as its own VOI. Logic 210 then generates a set of PE candidates, and their locations, within each VOI.

According to one embodiment, the set of PE candidates may be generated using the Toboggan algorithm (J. Fairfield. Toboggan contrast enhancement for contrast segmentation. In *Proceedings of the 10th IEEE International Conference on Pattern Recognition*, volume 1, pages 712-716, September 1990). In one embodiment, the Toboggan algorithm can scan the entire image, or a volume of interest (VOI) within the entire image. In another embodiment, the Toboggan algorithm can be initiated at a locus provided by an operator, such as a radiologist. Embodiments of the invention that employ the Toboggan algorithm for PE candidate generation can produce as output, in addition to the PE candidate locations, a set of volume elements ("voxels") that comprise each PE candidate, at logic step 215. The set of voxels that comprise a PE candidate may be referred to as a segment S, or as a region, or a segmented region, for PE candidate c. $S_c$ denotes, then, the segment or segmented region S in the image or in a VOI of the image, in which the Toboggan algorithm identifies a PE candidate c. Logic 220 then estimates, for each PE candidate c in the set of PE candidates, an orientation of the blood vessel that contains the PE candidate c (the "containing vessel"). Alternatively, logic 220 estimates, for each PE candidate c in the set of PE candidates, an orientation of the VOI in blood vessel that contains the PE candidate.

A voxel represents a value on a regular grid in three-dimensional space. As with picture elements ("pixels") in a bitmap, voxels themselves do not typically have their position (their coordinates) explicitly encoded along with their values. Instead, rendering systems may infer the position of a voxel based upon its position relative to other voxels (i.e., its position in the data structure that makes up a single volumetric image). In an alternative embodiment, points or polygons may be used to identify each PE candidate. In contrast to pixels and voxels, points and polygons may be explicitly represented by the coordinates of their vertices, thereby efficiently representing simple 3D structures with lots of empty or homogeneously filled space, whereas voxels are better at representing regularly sampled spaces that are non-homogeneously filled. A voxel represents a single sample, or data point, on a regularly spaced, three-dimensional grid. This data point can consist of a single piece of data, such as an opacity, or multiple pieces of data, such as a color in addition to opacity. A voxel represents only a single point on this grid, not a volume. The space between each voxel is not represented in a voxel-based dataset. Depending on the type of data and the intended use for the dataset, this missing information may be reconstructed and/or approximated, e.g. via interpolation. The value of a voxel may represent various properties. In CT scans, the values are Hounsfield units (HUs—a quantitative scale for describing radiodensity or radiopacity), giving the opacity of a material. An HU may also be referred to as a CT number. Different types of value are used for other imaging techniques such as MRI or ultrasound.

Figure 3:
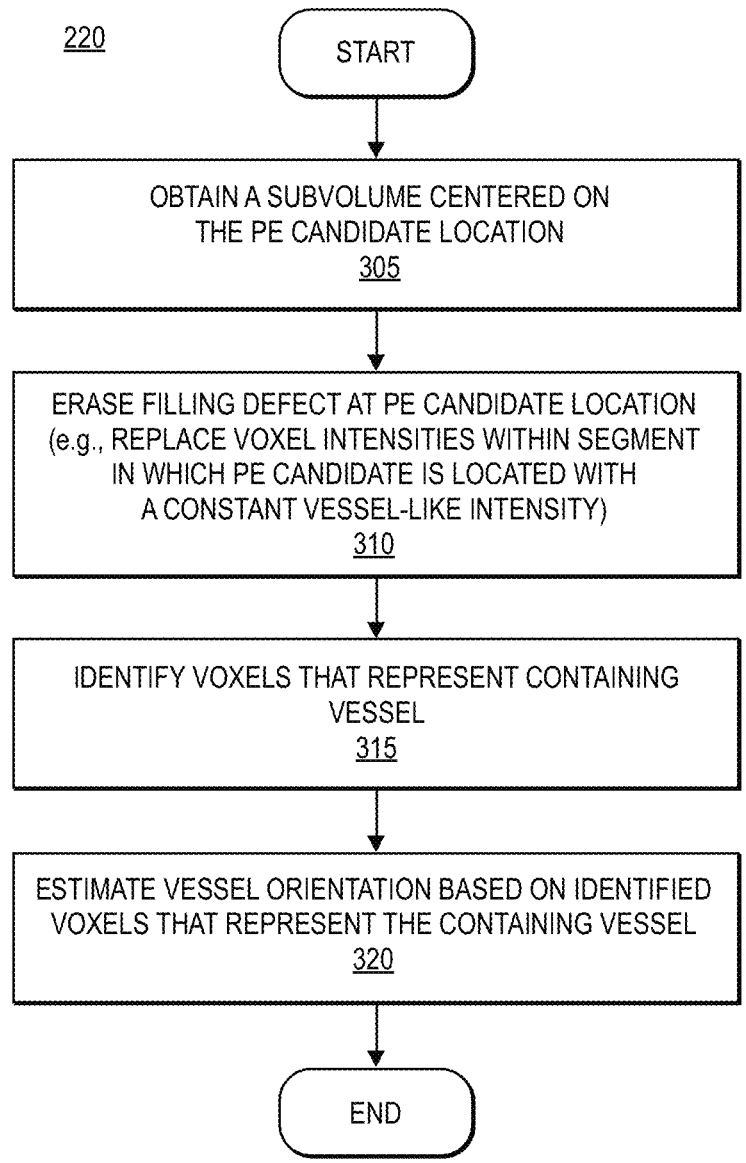
FIG. 3 is a flow chart relating to estimating an orientation of a blood vessel in accordance with an embodiment of the invention.
Figure 4:
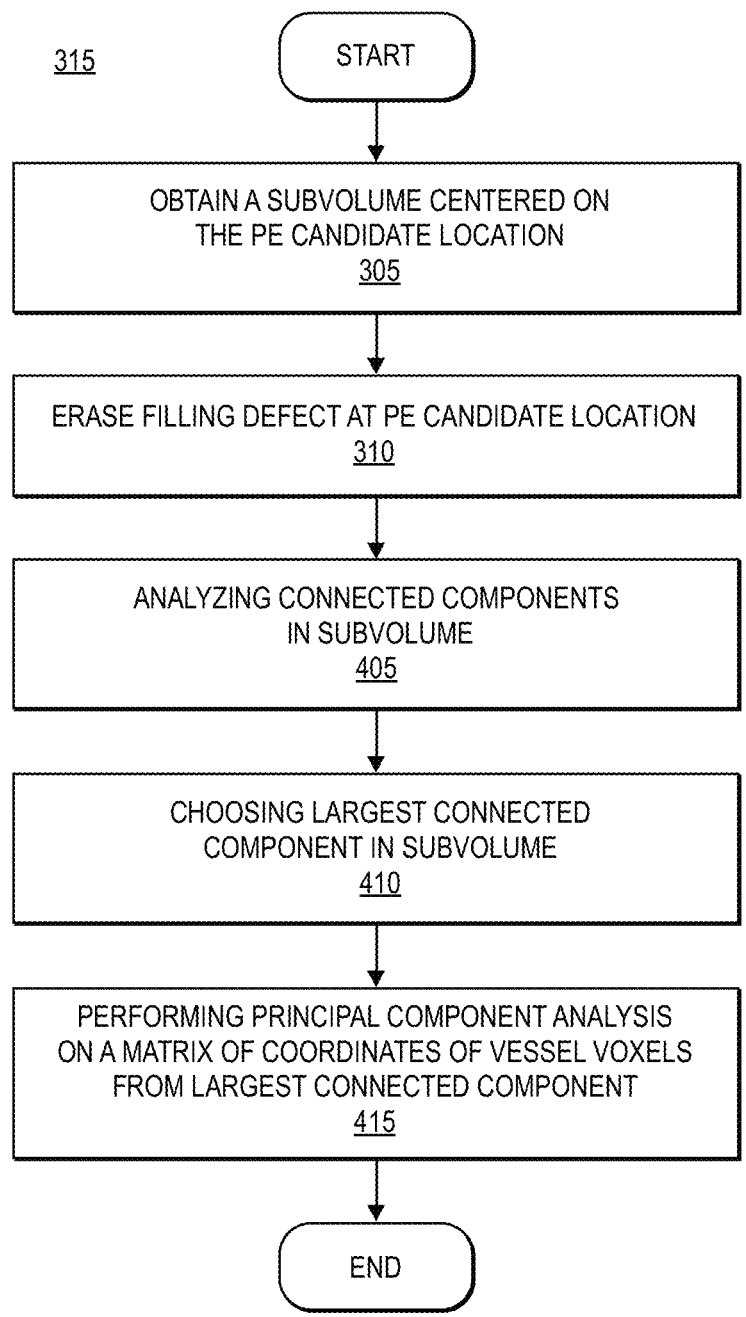
FIG. 4 is a flow chart relating to aspects of estimating an orientation of a blood vessel in accordance with an embodiment of the invention.

With reference to FIG. 3, according to an embodiment, logic 220 for estimating the orientation of the vessel involves the following logic. To estimate the orientation of the blood vessel containing the PE candidate c (the "containing vessel"), logic 305 first extracts a subvolume centered on the location of the PE candidate c, according to the equation $V_c=V(c_x-i, c_y-j, c_z-k)$ where i, j, k are determined according to the physical size of the subvolume. Logic 310 then replaces voxel intensities within the segment $S_c$ with a constant vessel-like intensity, such as a voxel intensity of 1100 HU, $V_c(x,y,z)=1100$ if $(x,y,z) \in S_c$. This has the effect of filling, or erasing, the filling defect at the location of the PE candidate c inside and on the surface of the containing vessel. Once the filling defect is filled, logic 315 identifies the voxels that represent the containing vessel (the "containing vessel voxels"). With reference to FIG. 4, the logic 315 for identifying the voxels that represent the containing vessel comprises logic 405 for analyzing the connected components in $V_c$ and logic 410 for choosing the largest connected component in $V_c$.

Figure 5:
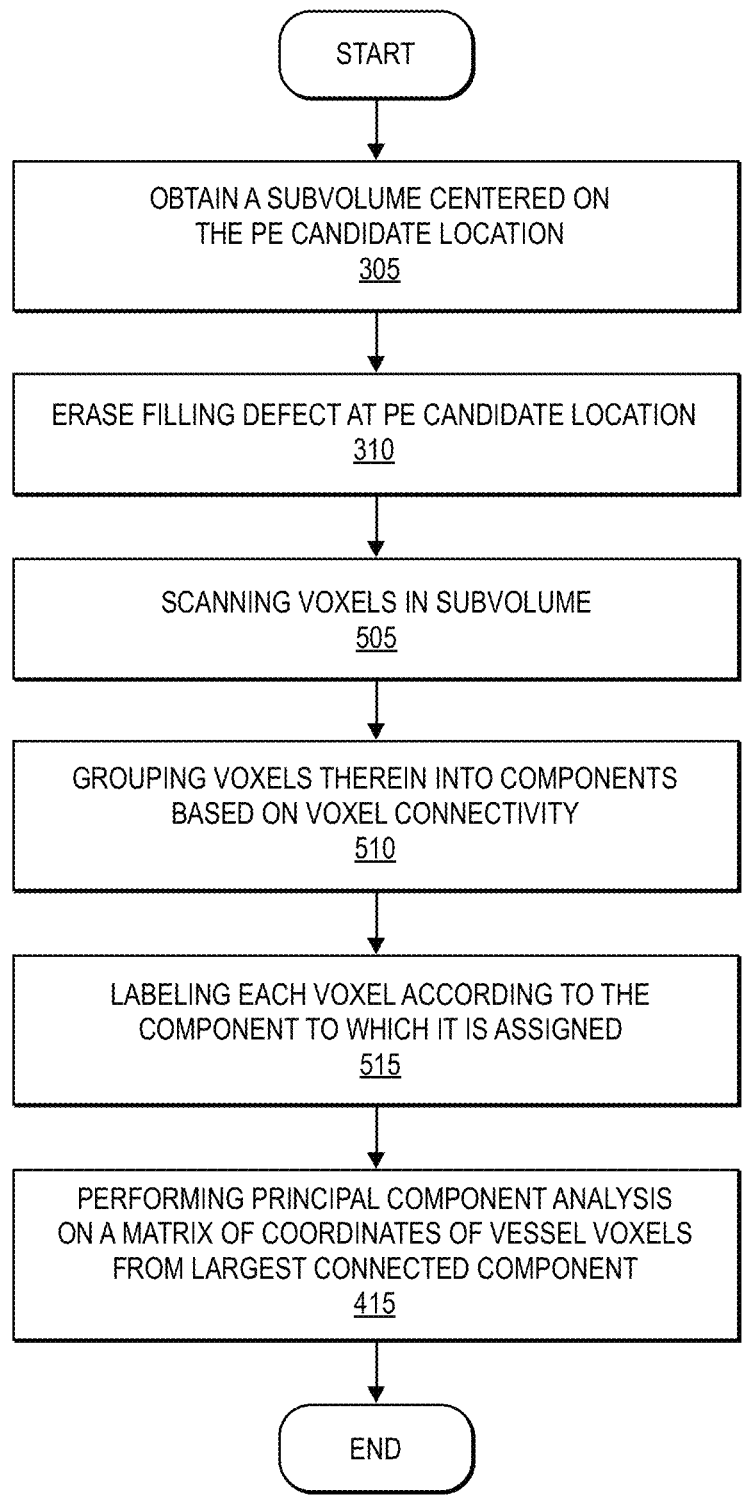
FIG. 5 is a flow chart relating to additional aspects of estimating an orientation of a blood vessel in accordance with an embodiment of the invention.

Logic 405 for analyzing the connected components and logic 410 for choosing the largest connected component involves, with reference to FIG. 5, logic 505 for scanning the voxels in $V_c$, and logic 510 for grouping/assigning the voxels therein into/to components based on voxel connectivity, i.e., all voxels in a connected component share similar voxel values, e.g., voxel intensity values, and/or are in some way connected with each other. Once all groups have been determined, each voxel may be labeled at logic step 515 according to the component to which it was assigned or into which it was grouped. Connected component labeling involves scanning the image, voxel-by-voxel, according to some sequence, in order to identify connected voxel regions, i.e., regions of adjacent voxels that share the same set of values, e.g., the same set of intensity values. Note that if the filling defect is not identified using the aforementioned approach, the voxels comprising the PE would be excluded from the largest connected component of the vessel, significantly altering the estimated shape of the vessel and hence the estimation of the vessel's orientation.

Referring again to FIG. 3, logic 320 then estimates the vessel's orientation based on the identified voxels that represent the containing vessel. With reference to FIG. 4, according to one embodiment, let $I_{n \times 3}$ denote a matrix that has in its rows the coordinates of the vessel voxels from the largest connected component. In such an embodiment, vessel orientation is computed by logic 415 performing a principal component analysis (PCA) on matrix I. Mathematically, the embodiment solves for $I^T I = \lambda_i \vec{v}_i$ where $\vec{v}_1$, $\vec{v}_2$, $\vec{v}_3$ are the eigen vectors of the analyzed component and $\lambda_1, \lambda_2, \lambda_3$ are the eigen values ($\lambda_1 > \lambda_2 > \lambda_3$). Because $\lambda_1$ is the largest eigen value, $\vec{v}_1$ determines the vessel orientation. Also, vectors $\{\vec{v}_1, \vec{v}_2\}$ or $\{\vec{v}_1, \vec{v}_3\}$ span planes that extend longitudinally through the vessel and the vectors $\{\vec{v}_2, \vec{v}_3\}$ span the plane that extends transversely across the vessel.

PE Candidate Visualization

Figure 6:
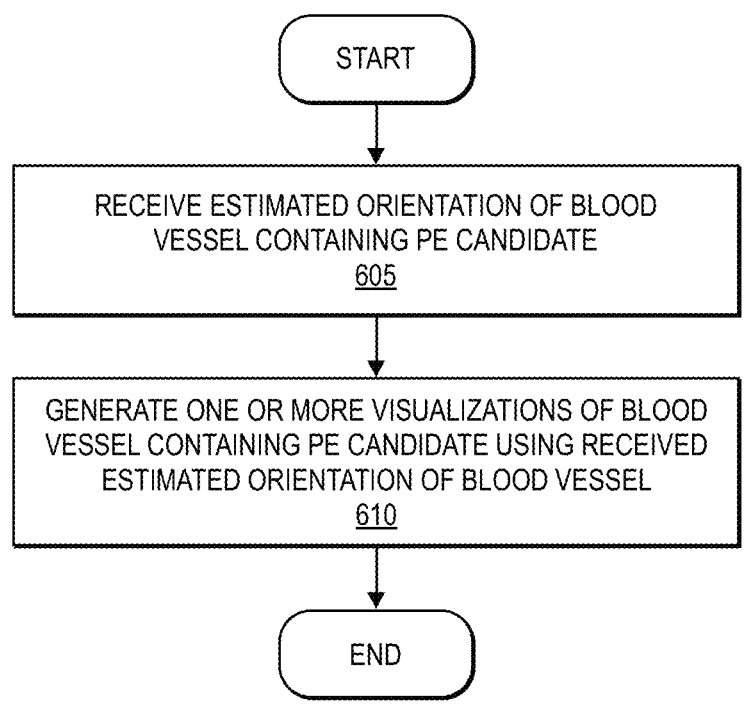
FIG. 6 is a flow chart relating to additional aspects of estimating an orientation of a blood vessel in accordance with an embodiment of the invention.

With reference to FIG. 6, embodiments of the invention 600 can generate visualizations of the blood vessel for display on a device (e.g., a computer screen visible to a radiologist) using the above-described estimated orientation of the blood vessel. For example, the system includes logic 605 to receive the estimated orientation of the blood vessel containing a PE candidate, and then logic 610 to generate a visualization of the blood vessel containing the PE candidate. According to one embodiment, the visualization involves determining a rotation matrix based on the orientation of the blood vessel, where the rotation matrix is parameterized by a rotation angle.

Given a PE candidate location selected by a radiologist or by a PE candidate location generation method, embodiments of the invention provide a PE visualization system that generates one or both of two animations for review. The first animation, referred to herein below as Animation I, shows how the z-axis rotates towards the vessel orientation, whereas the second animation, referred to herein below as Animation II, visualizes the filling defect from multiple perspectives after the vessel axis is aligned with the y-axis of a 2D display window.

Animation I: Axis Alignment

The first animation is generated according to Euler's rotation theorem which states that, in a three-dimensional (3D) space, any two Cartesian coordinate systems with the same origin are related by a rotation about some fixed axis $\vec{K}$ at some degree of angle $\theta$:

$$\theta = \arccos\left(\frac{r_{11} + r_{22} + r_{33} - 1}{2}\right). \quad (1)$$

$$\vec{K} = \begin{bmatrix} k_x \\ k_y \\ k_z \end{bmatrix} = \frac{1}{2\sin\theta} \begin{bmatrix} r_{32} - r_{23} \\ r_{13} - r_{31} \\ r_{21} - r_{12} \end{bmatrix} \quad (2)$$

Where $r_{ij}$ are the entities of matrix R computed as $R = A^T A'$ with A denoting a rotation matrix that maps a global coordinate system to a coordinate system of the volumetric (CT) image and A' denoting a rotation matrix that maps the global coordinate system to a coordinate system defined by the orientation of the blood vessel. The rotation matrix parameterized by the rotation angle $\phi$ may be defined by:

$$\begin{bmatrix} k_xk_x(1-\cos\phi)+ & k_yk_x(1-\cos\phi)- & k_zk_x(1-\cos\phi)+ \\ \cos\phi & k_z\sin\phi & k_y\sin\phi \\ k_xk_y(1-\cos\phi)+ & k_yk_y(1-\cos\phi)+ & k_zk_y(1-\cos\phi)- \\ k_z\sin\phi & \cos\phi & k_x\sin\phi \\ k_xk_z(1-\cos\phi)- & k_yk_z(1-\cos\phi)+ & k_zk_z(1-\cos\phi)+ \\ k_y\sin\phi & k_x\sin\phi & \cos\phi \end{bmatrix}$$

The above equation shows the rotation matrix for an arbitrary intermediate angle φ (0 φ θ), yielding the intermediate display axes $A^\varphi = AR^\varphi$, from whose x-y plane, a new image is reformatted for display, resulting in a "rotating" effect with φ running from 0 to θ.

With the availability of $\vec{K}$ and θ, and the rotation matrix parameterized by the rotation angle φ, a rotation about axis $\vec{K}$ a can be animated by gradually changing the rotation angle from 0 to θ. More specifically, for each rotation angle in a sequence of rotation angles between 0 and θ, an intermediate coordinate system defined by: $A^\varphi = AR^\varphi$ can be determined, and a rotated planar image depicting the blood vessel can be obtained as the (x,y) plane of the intermediate coordinate system. Each rotated planar image depicting the blood vessel can be displayed on a display of a device (e.g., on a computer screen visible to a radiologist), thereby generating a visualization. The rotated planar image obtained as the (x,y) plane of the intermediate coordinate system corresponding to rotation angle θ (i.e., the "terminal rotation angle") depicts the blood vessel along the longitudinal axis of the blood vessel.

Figure 10:
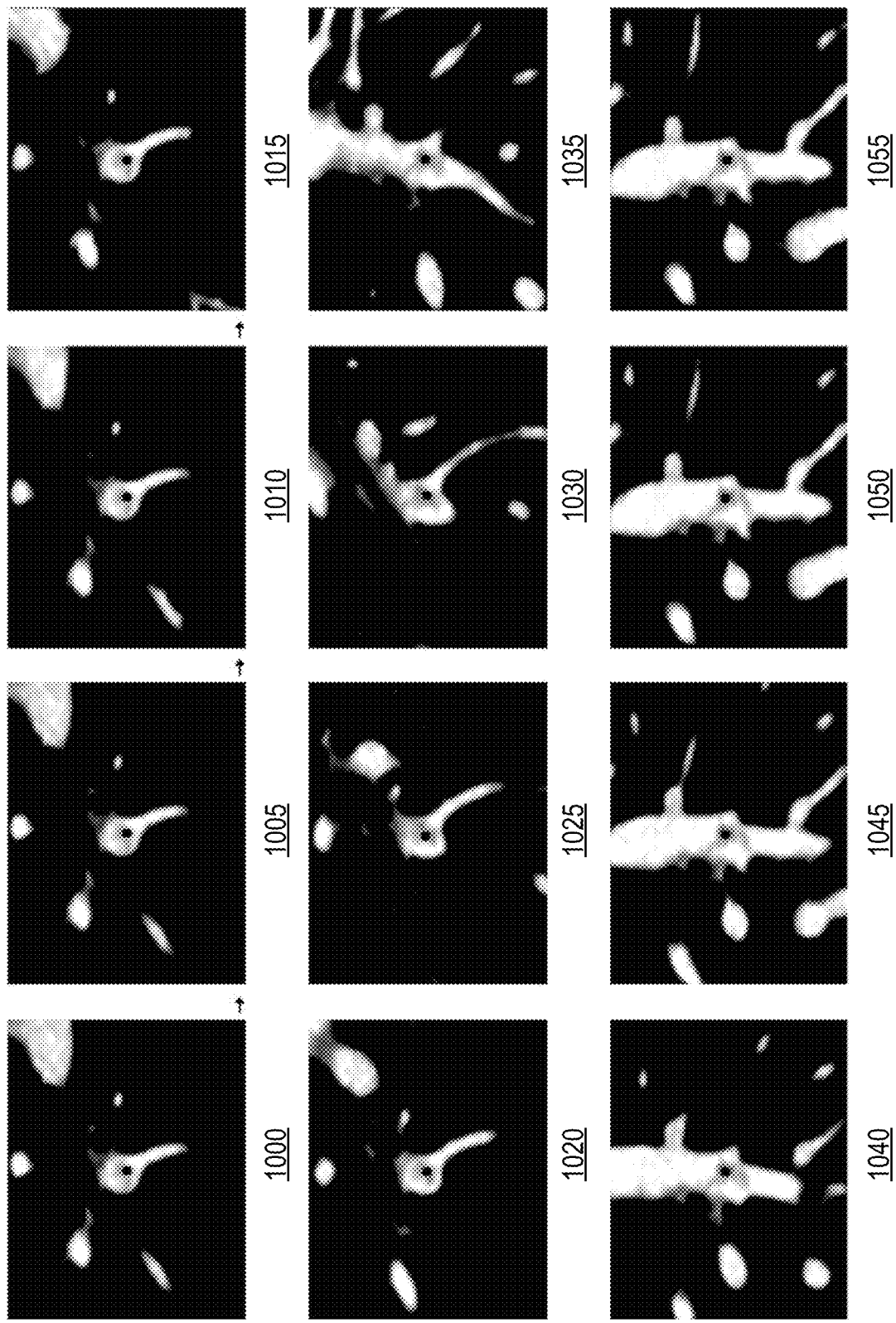
FIG. 10 illustrates an animation according to an embodiment of the invention.
Figure 11:
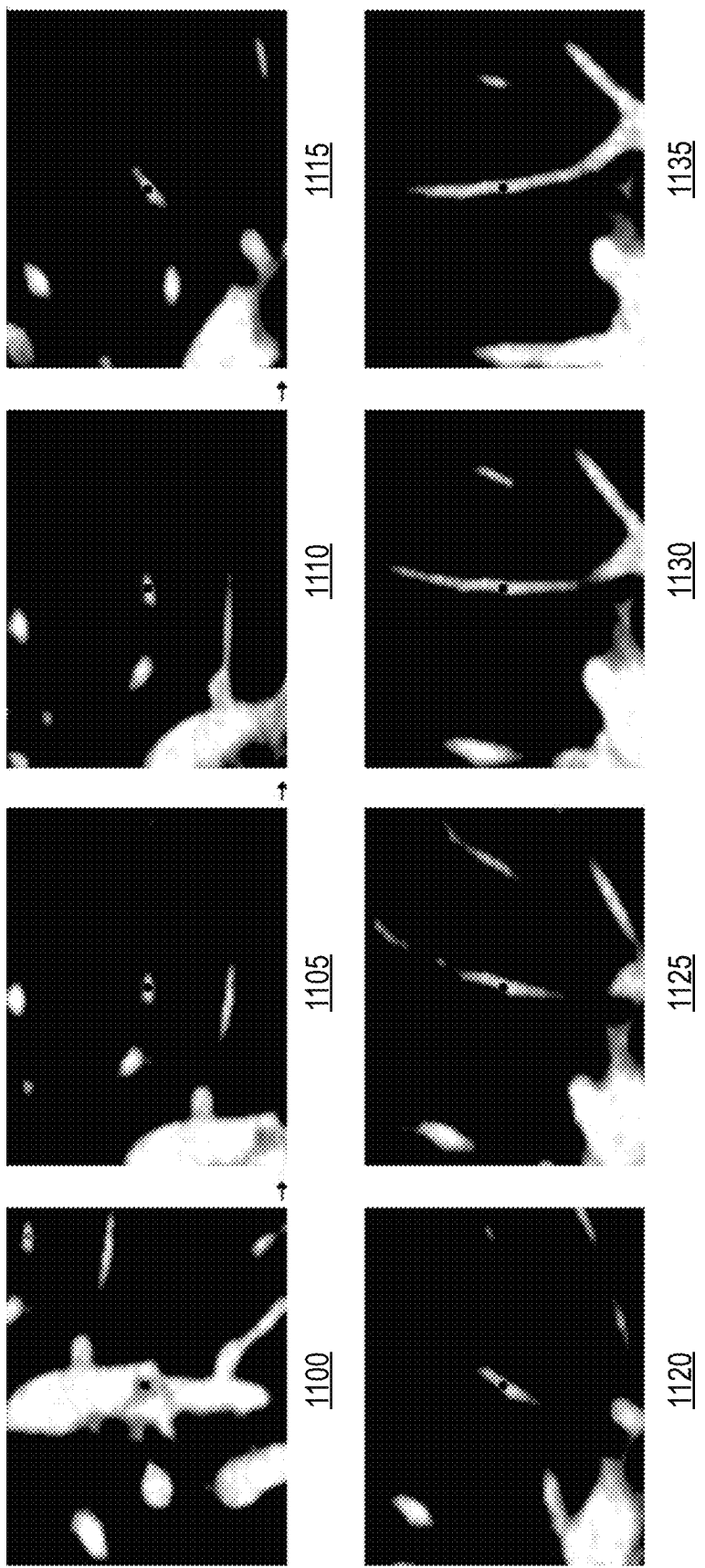
FIG. 11 illustrates an animation according to an embodiment of the invention.

As an example, assume a radiologist clicks (selects) a location indicated by the black dot in the center of image plane 1000 illustrated in FIG. 10, an embodiment then generates a new image plane as shown in 1040, whereby the longitudinal axis of the vessel is aligned with the vertical centerline of the display window. The embodiment may also generate a movie that shows the transition between the two frames. Image planes 1005-1035 show a few intermediate frames. The user also has the freedom to select a new location for further inspection by following the same vessel branch or jumping to a different vessel branch. An illustration of axis alignment in the animation as described herein is provided in FIG. 11. For example, during the examination process, if the user clicks the location indicated by the black dot in the center of image frame 1100 in FIG. 11, the embodiment will move this new location to the center of the image plane as shown at 1105 and then automatically rotate the vessel axis to align with the vertical centerline for inspection, as shown in the image plane at 1135. In this example, the vessel is free of PE.

Animation II: 360-Degree Tour

Figure 12:
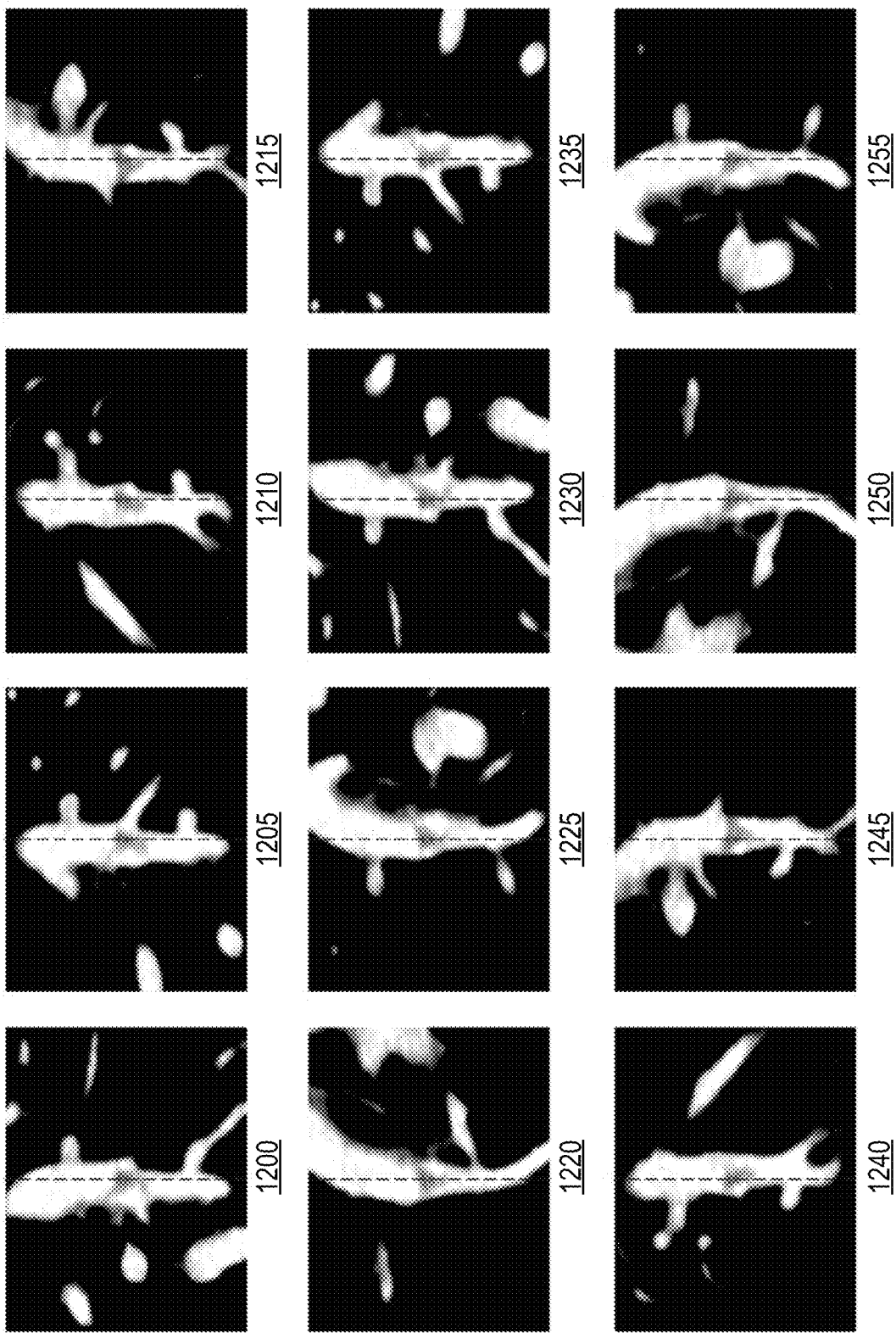
FIG. 12 illustrates an animation according to an embodiment of the invention.

The second animation allows a 360-degree tour of the filling defect and the vessel that contains the PE while maintaining alignment of the vessel with the vertical axis of the display window. Each animated frame is constructed by interpolating the CT volume along $\vec{v}_1$ and $\vec{v}_2^\theta$ where $\vec{v}_1$ denotes the vessel axis and $\vec{v}_2^\theta$ denotes a rotation of $\vec{v}_2$ by angle θ around the vessel axis, $\vec{v}_2^\theta = \vec{v}_2 \cos\theta + (\vec{v}_1 \times \vec{v}_2)\sin\theta + \vec{v}_1(\vec{v}_1 \cdot \vec{v}_2)(1-\cos\theta)$. FIG. 12 shows frames 1200-1255 from the 360-degree tour, in which once the longitudinal axis is aligned with the vertical centerline, an embodiment will starting rotating around the vertical line, providing a compelling demonstration of the filling defect.

PE Candidate Classification

Although vessel orientation $\vec{v}_1$ can be uniquely obtained for each PE candidate, there exists no unique pairs of {$\vec{v}_2$, $\vec{v}_3$} that can span the cross-sectional plane. In fact, any pair {$\vec{v}_2^\theta$, $\vec{v}_3^\theta$} can serve the purpose where $\vec{v}_2^\theta$ and $\vec{v}_3^\theta$ are computed by rotating $\vec{v}_2$ and $\vec{v}_3$ around vessel axis, $\vec{v}_1$, by θ degrees using Rodrigues' rotation formula:

$$\vec{v}_2^\theta = \vec{v}_2 \cos\theta + (\vec{v}_1 \times \vec{v}_2)\sin\theta + \vec{v}_1(\vec{v}_1 \cdot \vec{v}_2)(1-\cos\theta)$$

$$\vec{v}_3^\theta = \vec{v}_3 \cos\theta + (\vec{v}_1 \times \vec{v}_3)\sin\theta + \vec{v}_1(\vec{v}_1 \cdot \vec{v}_3)(1-\cos\theta)$$

Therefore, and with reference to FIG. 7, embodiments of the invention obtain two imaging plane envelopes. The first envelope, $E_{cross}$ 732, contains the cross sectional image planes 720, spanned by {$\vec{v}_2^\theta$, $\vec{v}_3^\theta$}, and the second envelope, $E_{long}$ 730, contains the longitudinal image planes 725 spanned by {$\vec{v}_1^\theta$, $\vec{v}_2^\theta$} or {$\vec{v}_1^\theta$, $\vec{v}_3^\theta$}. To generate a 3-channel image presentation for a PE candidate, one embodiment randomly selects one image plane 740 from $E_{cross}$ and two image planes 741 and 742 from $E_{long}$. The resulting image patch shows the PE candidate from one cross sectional view of the vessel and two longitudinal views of the vessel.

Experiments

To evaluate the effectiveness of the image representation for PE diagnosis according to embodiments of the invention, experiments were conducted in which 121 CTPA datasets with a total of 326 emboli were used. Image representation according to embodiments of the invention were compared with two other alternative image representation schemes, namely a 2.5D image representation scheme, and a standard clinical representation scheme consisting of sagittal, coronal, and axial views. For a comprehensive comparison between the three image representations, six CNN architectures of varying depths were used, which were trained using 100%, 50%, and 25% of the available labeled training data. The experiments demonstrated that the image representation according to embodiments of the invention allowed for fast training of a high-performing CAD system, even in the absence of deep architectures and large labeled training sets—factors whose absence are highly detrimental to the other two image representations. A CAD system operating in accordance with the embodiments also outperformed the winning system from the PE challenge at 0 mm localization error, although the embodiments were outperformed at 2 mm and 5 mm localization errors. However, optimizing performance at 0 mm localization error provides greater advantage for clinical applications than greater performance at 2 mm and 5 mm localization errors.

PE Candidate Generation

As with other PE CAD systems, candidate generation is the first stage of a PE diagnosis system in accordance with embodiments of the invention. Embodiments of the invention employ a straightforward candidate generation method, comprising the steps of lung segmentation followed by application of the Toboggan algorithm.

According to an embodiment, a simple and heuristic lung segmentation method may be used. Given a CT dataset, voxel intensities are clipped using an intensity threshold in order to identify the regions with low intensity values. This thresholding scheme results in a binary volume wherein the lung area and other dark regions in the volume appear white. The embodiment then performs a closing operation to fill the holes in the white volume. To exclude non-lung areas, a 3D connected component analysis is performed and components with small volumes or with large length ratio between the major and minor axes are removed. The Toboggan algorithm is then applied only to the lung area, generating the PE candidates which are used as input to different image representations.

A PE candidate generation method according to an embodiment of the invention was applied to a database of 121 CTPA datasets with a total of 326 emboli, producing 8585 PE candidates, of which 7722 were false positives and 863 were true positives. It is possible to produce multiple detections for a single large PE and that explains why the number of true detections is greater than the number of emboli in the database. According to the available ground truth, the candidate generation module achieves a sensitivity of 93% for PE detection while producing, on average, 65.8 false positives per patient. For the remainder of this description, the emboli missed by the candidate generation method are ignored, which allows one to obtain a sensitivity of 100% if at least one candidate per detected PE is labeled correctly. To use entire database, each image representation is evaluated in a 3-fold cross validation scenario after splitting the database into three separate subsets at the patient-level.

False Positive Reduction

For false positive reduction, six CNN architectures of various depths were trained: a shallow CNN (sh-CNN) with one convolutional layer; the LeNet architecture; a relatively deep CNN (rd-CNN) with four convolutional layers whose deviations are commonly used in medical imaging applications, and three deeper CNN architectures named AlexNet, VGG, and GoogleNet. For AlexNet, VGG, and GoogleNet architectures, experiments chose to fine-tune pre-trained models available in the Caffe model zoo rather than train them from scratch. This choice is motivated by previous work wherein it was demonstrated that fine-tuned deep architectures outperform or, in the worst case, perform comparably to the counterpart CNNs trained from scratch. The pre-trained models used in the experiments have been trained using 1.2 million images labeled with 1000 semantic classes. Note that no pre-trained models are available for shallower architectures; therefore, the experiments train sh-CNN, rd-CNN, and LeNet from scratch after initializing the convolutional layers using Xavier's method. The experiments show that this technique gives consistently greater performance than random weight initialization using Gaussian distributions. To avoid under-training and over-training, a validation set was created by selecting 20% of the training set at the patient-level and then monitored the AUC of the task of candidate classification on the validation set during the training stage. For each architecture, the training process continued until either the AUC saturated or the AUC began decreasing. The above CNN architectures were trained using the Caffe library.

For comparison, the experiments trained the above CNN architectures for two additional image representations, namely the standard image representation consisting of conventional clinical views at a given candidate location, and a 2.5D approach, as explained herein. To ensure fair comparisons between the image representations, the experiments used the same candidate generator algorithm followed by the same amount of data augmentation.

Figure 17:
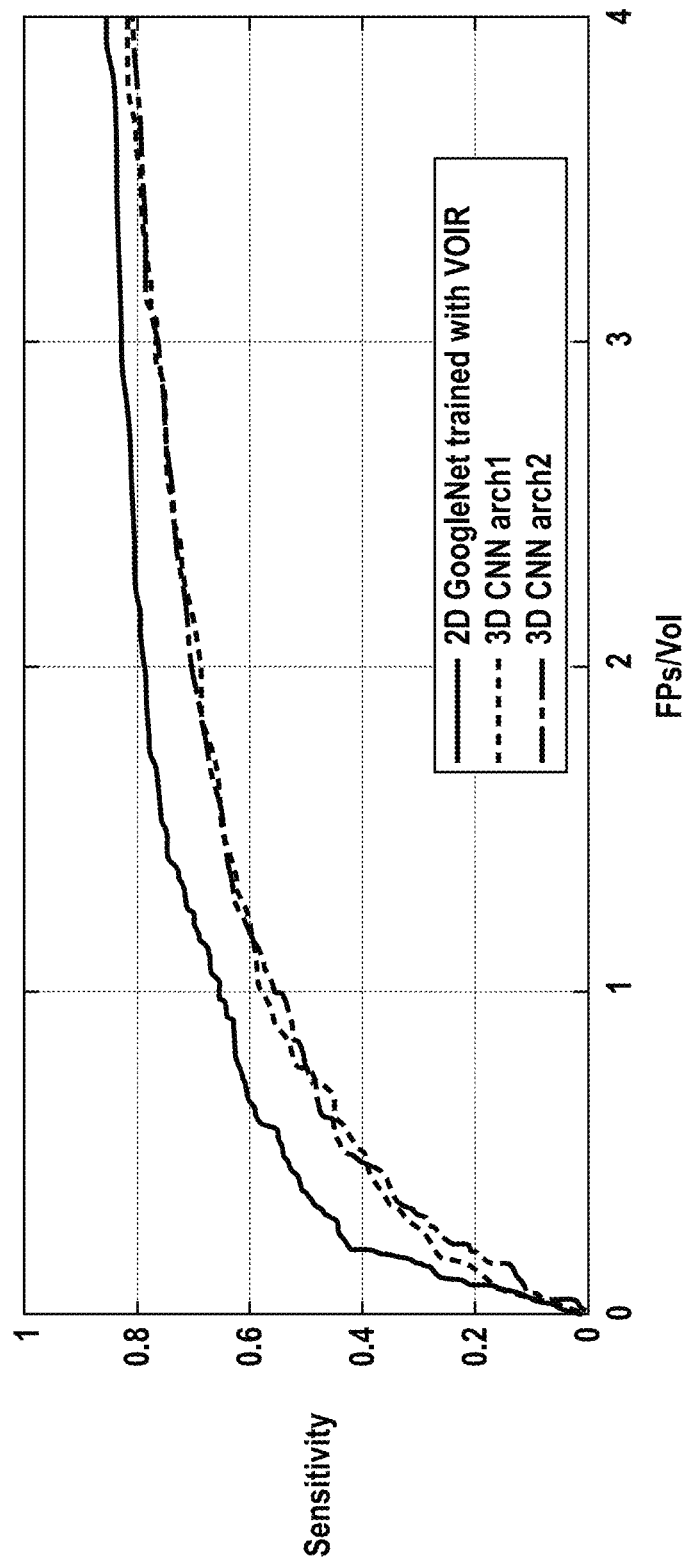
FIG. 17 provides a graphical comparison between 2D image representation according to embodiments of the invention and 3D image representation.

With reference to FIG. 17, experiments further compared the 2D representation according to embodiments of the invention (VOIR) with the 3D image representation for the task of false positive reduction. For this purpose, a 3D ResNet-18—a residual network with 18 convolutional layers (architecture 2 ("arch2") in FIG. 17), and an 8-layer 3D CNN (architecture 1 ("arch1") in FIG. 17) were trained using 3D subvolumes around PE candidates. Since both architectures tended to overfit, the experiments used heavy data augmentation including translation, scale, and rotation during training. FIG. 17 shows the resulting FROC curves. The JAFROC analysis shows that the GoogleNet trained with embodiments of the invention (VOIR) significantly outperforms the 3D models (p<.001).

Overall Performance Evaluation

Figure 13A:
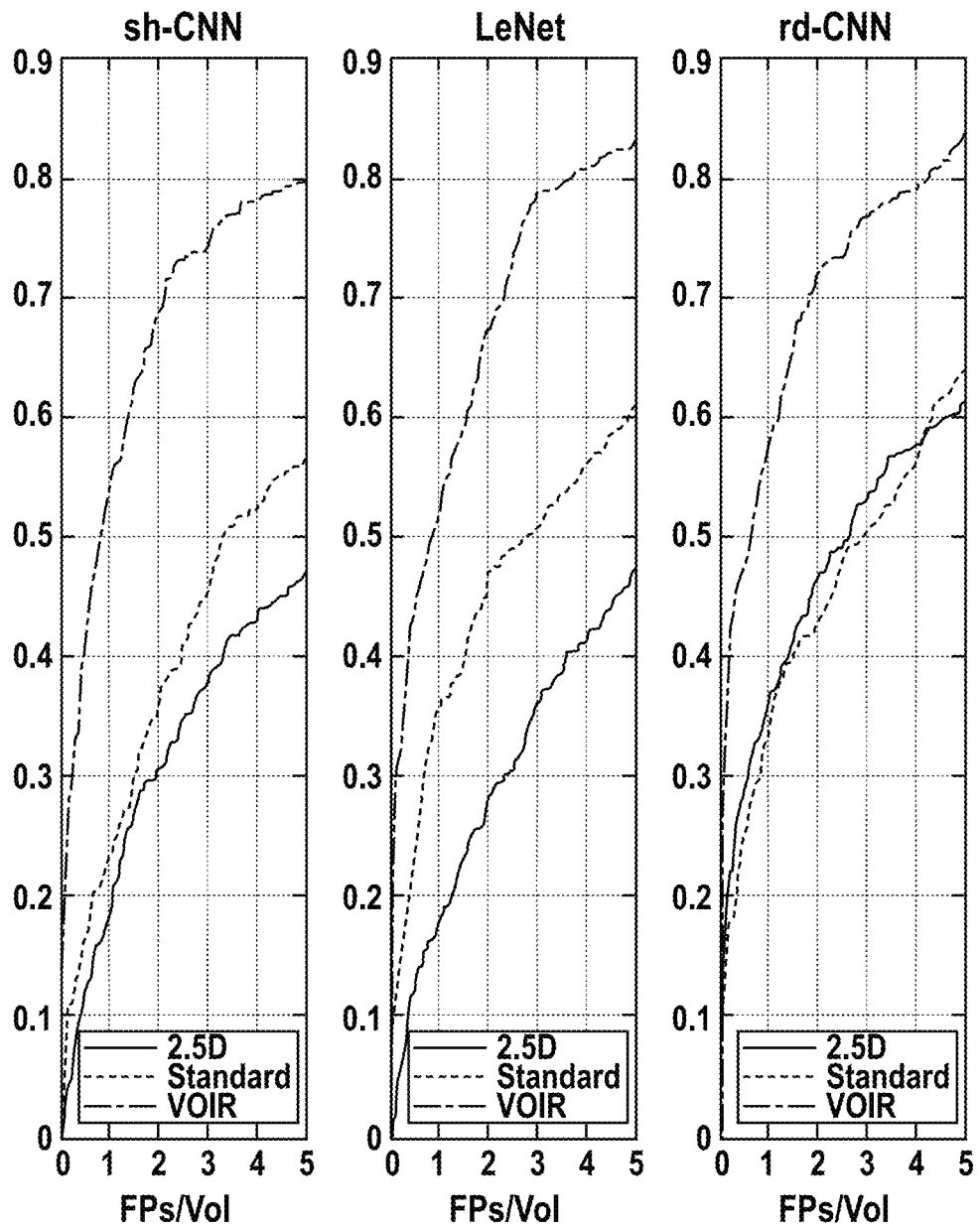
FIGS. 13A and 13B are a graphic depicting FROC analysis for different image representations grouped by architecture, including an embodiment of the invention.
Figure 13B:
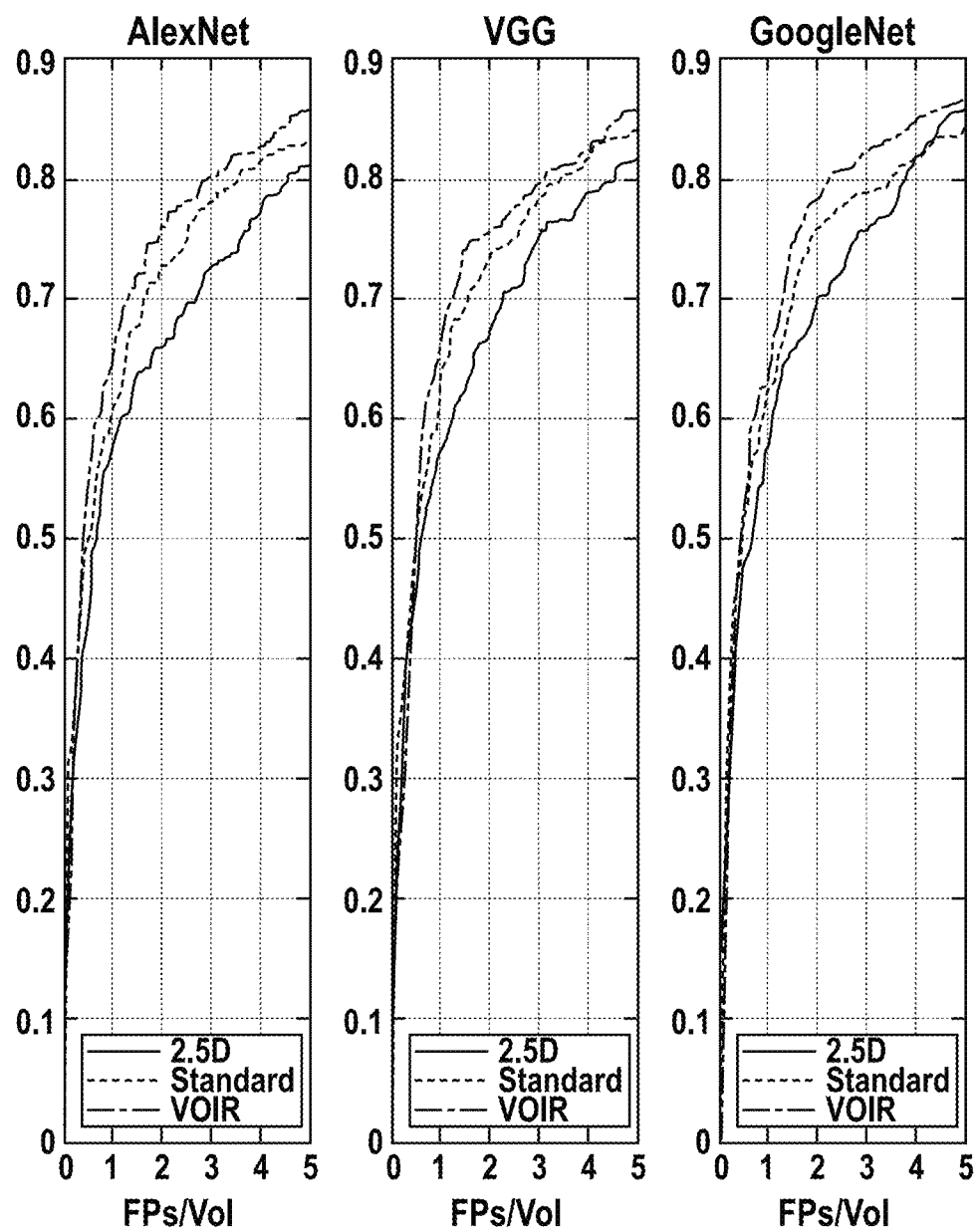

The experiments trained and evaluated 54 CNNs (three image representations times six architectures times three folds). FIGS. 13A and 13B show the free-response receiver operating characteristic (FROC) curves grouped by architecture, and demonstrates that the impact of image representation on model performance depends on architecture depth, with shallower architectures benefiting most from a strong image representation. The performance gap caused by the choice of image representation is, however, closed to some extent using deeper architectures. Jackknife alternative FROC (JAFROC) analysis indicates that the difference between embodiments of the invention for image representation (VOIR) and standard image representation is not significant in the case of AlexNet and VGGNet, although the gap widens in the case of GoogleNet. From FIGS. 13A and 13B, it is also observed that the standard image representation, in most cases, yields higher performance than the 2.5D approach.

Figure 14:
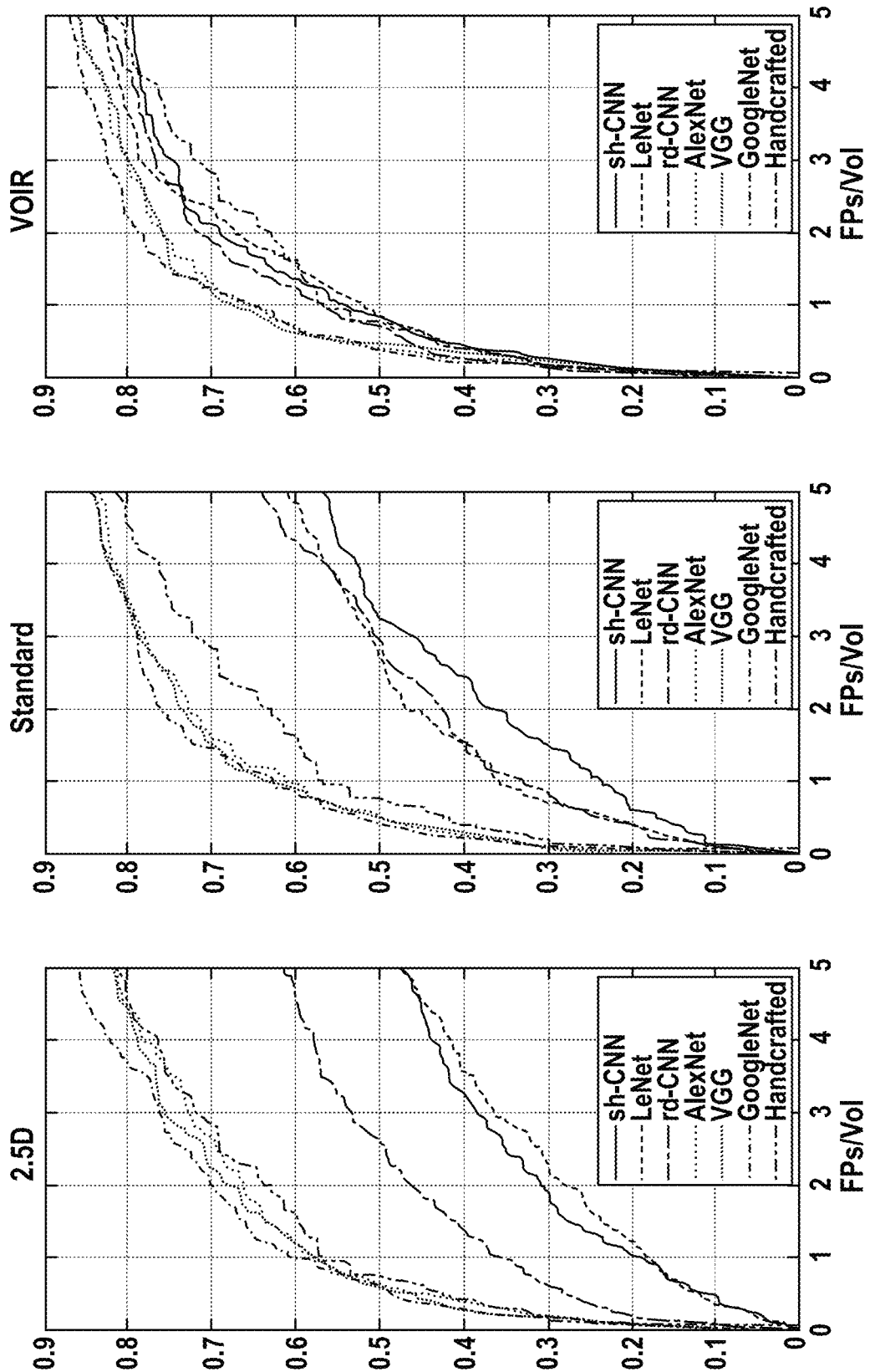
FIG. 14 is a graphic depicting FROC analysis for different image representations grouped by image representation, including an embodiment of the invention.

FIG. 14 shows the same FROC curves grouped by image representation. The use of deeper architectures in the case of standard and 2.5D image representation is highly effective, yielding substantial performance improvement over the shallower models. However, in the case of embodiments of the invention (VOIR), significantly lower performance gains are realized when shallower models are replaced with deeper architectures. This is because the inventive image representation leaves an easier problem for the convolutional models to solve; therefore, the performance gap between the deep and shallow models is not as wide. These results demonstrate the descriptive power of the image representation and its robustness to the choice of model architecture for embodiments of the invention.

To establish baseline performance, FIG. 14 also includes the performance curve of a "handcrafted" method that generates a set of PE candidates using an improved Toboggan algorithm and then reduces the false positives by a specialized multi-instance classifier trained using a variety of carefully handcrafted shape and texture features. Not surprisingly, all the deep architectures, regardless of image representation, outperform the handcrafted approach. However, interestingly, the handcrafted approach outperforms shallower architectures if the latter are trained using standard or 2.5D image representation.

Embodiments of the invention have also evaluated using the entire 20 CTPA test datasets from the PE challenge (www.cad-pe.org). Embodiments of the invention also outperformed the winning system from the PE challenge at 0 mm localization error, although an embodiment was outperformed at 2 mm and 5 mm localization errors. However, optimizing performance at 0 mm localization error provides greater advantage for clinical applications than greater performance at 2 mm and 5 mm localization errors.

Size of Training Set

Figure 15A:
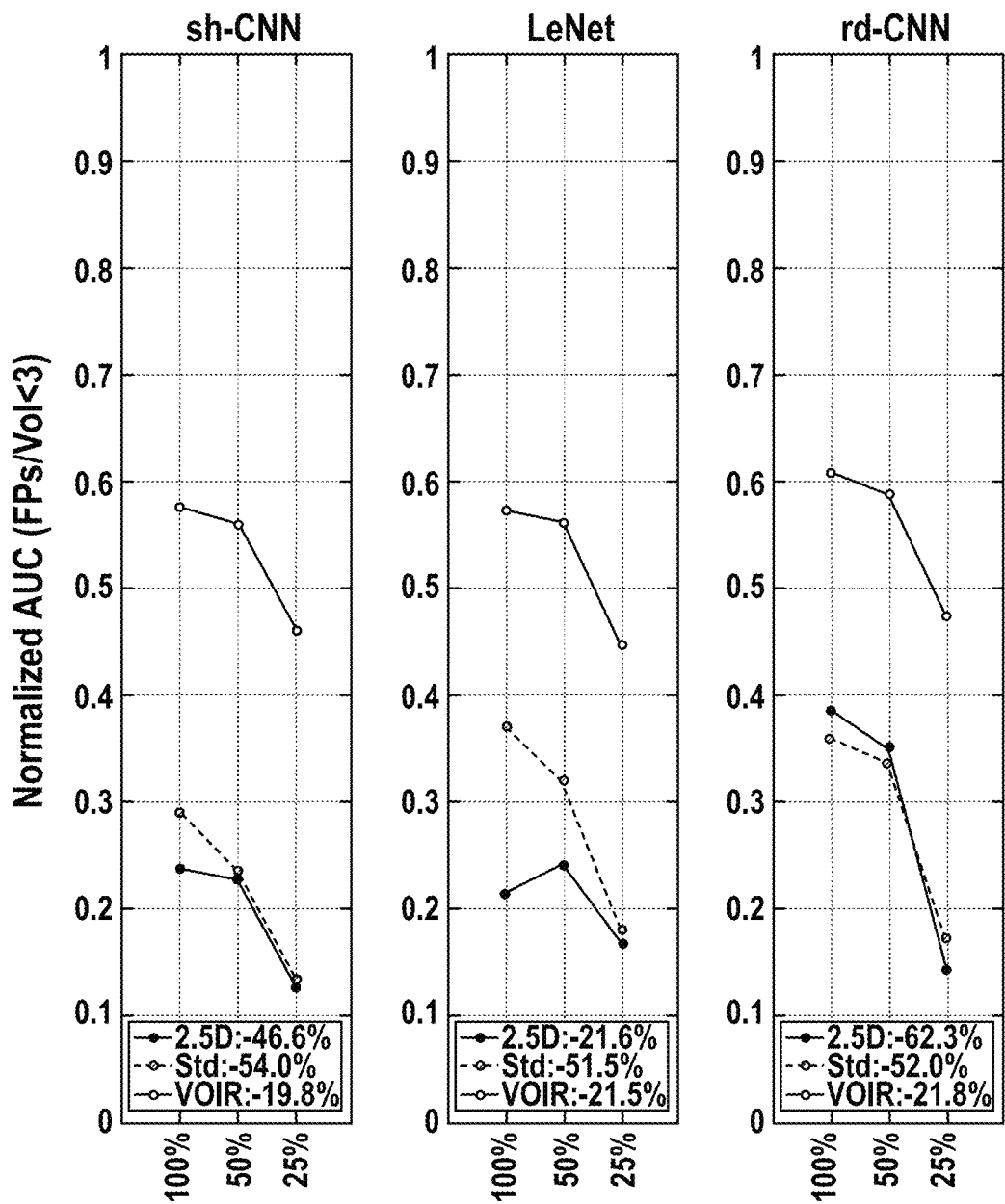
FIGS. 15A and 15B are a graphic that depicts the normalized area under FROC curve (FPs/Vol<3) when 100%, 50%, 25% of training data are used for training different architectures, including an embodiment of the invention.
Figure 15B:
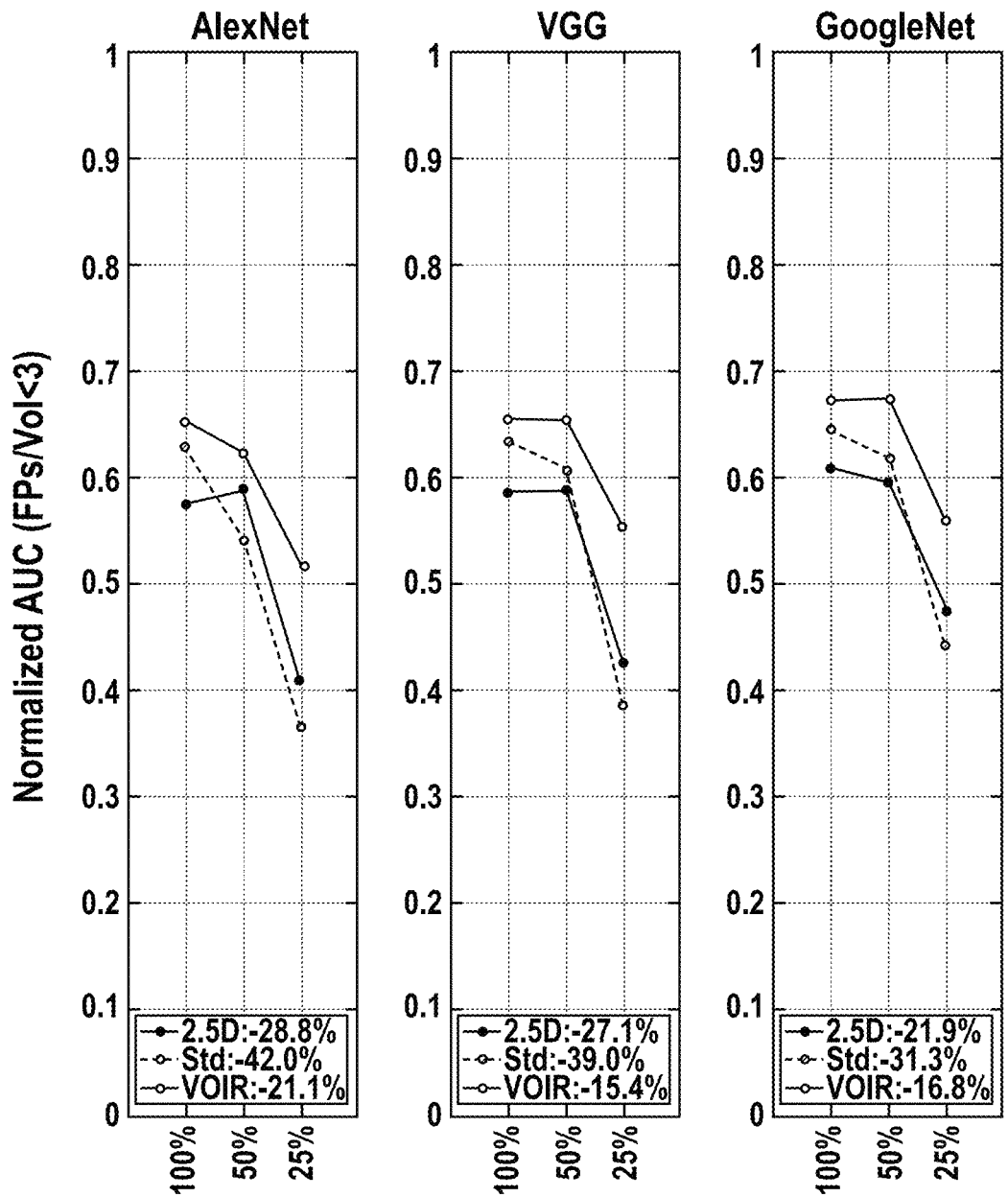

Adequately labeled training data is not always available for medical vision tasks. It is therefore important to evaluate the robustness of the image representations and architectures under study against the size of the training set. For this purpose, experiments involved re-training the architectures after reducing the training set by 50% and 25% at the patient-level, and then computing the normalized partial area under each FROC curve (normalized pAUC) up to three FPs/Vol. The results are shown in FIGS. 15A and 15B. To facilitate comparison among different image representations, the legends include the change in normalized pAUC when the training set is reduced to 25%. As seen, the embodiments of the invention (VOIR) show the highest level of robustness (smallest drop in normalized pAUCs) against the size of the training set across the architectures of varying depths. Also, it is evident that deeper architectures trained using standard and 2.5D image representations with 25% of the training set outperform the shallower counterparts trained with the entire training set. This can be attributed to the embedded knowledge transferred from the ImageNet database.

Speed of Convergence

Figure 16:
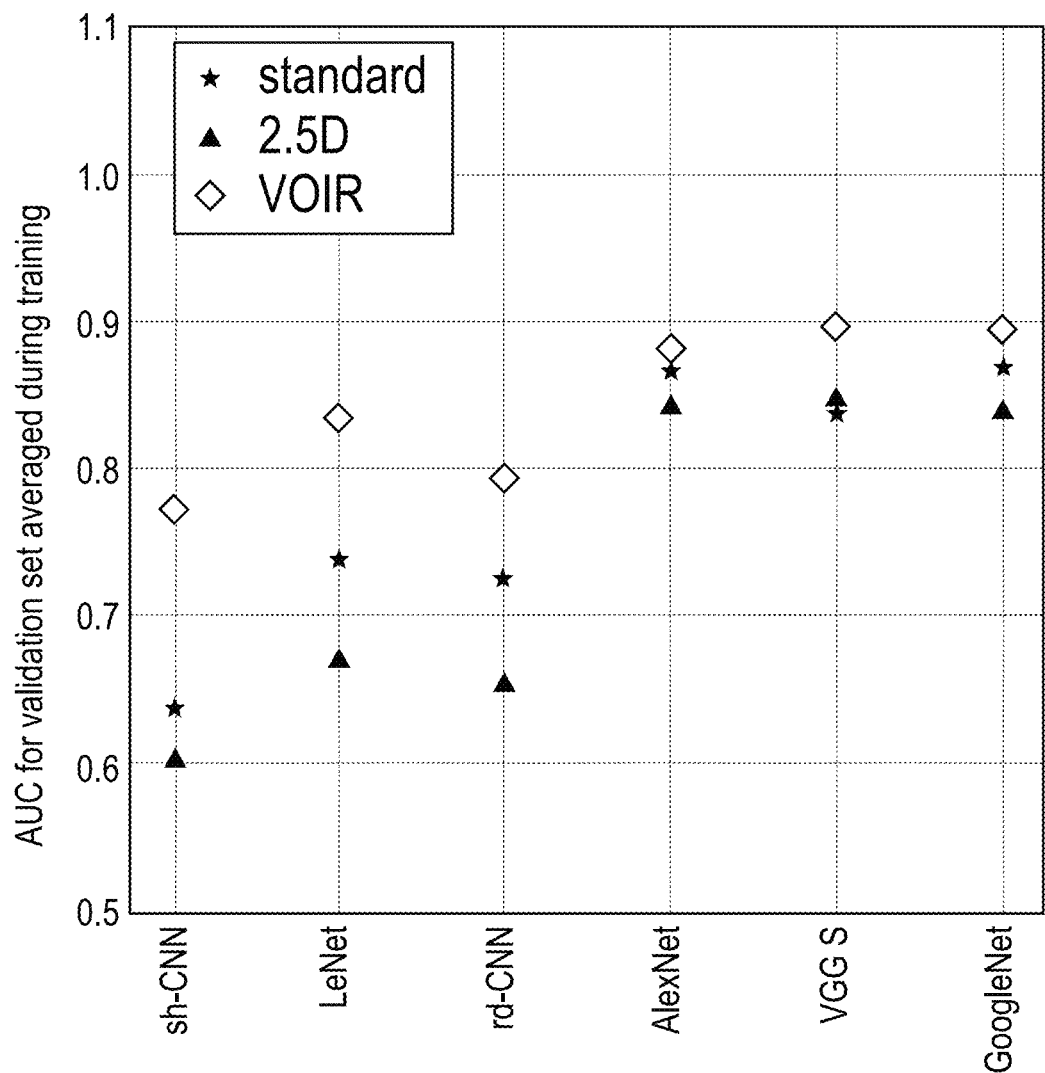
FIG. 16 is a graphic depicting convergence speed comparison among different image representations across various architectures, in which a large average AUC indicates faster convergence, including an embodiment of the invention.

How the choice of image representation impacts the speed of convergence for the architectures used in the experiments was investigated. For this purpose, the intermediate models were saved during the training stage and then each model evaluated using the validation set by computing the area under the ROC curve. The speed of convergence was measured by averaging the AUCs of the intermediate models. The average AUC is, in fact, related to the area under the convergence curve, which is a 2D plot that has iteration numbers on the horizontal axis and the AUC at each iteration on the vertical axis. The higher the area under the convergence curve, the faster the convergence. FIG. 16 compares the speed of convergence for each architecture and image representation. As seen, embodiments of the invention (VOIR) perform consistently better than the other two image representations. Furthermore, the superiority of VOIR over other representations is more pronounced for shallower architectures. This trend makes sense because deeper architectures start from a pre-trained model; thus, their convergence speed is less affected by the choice of image representation.

Other Image Representations

Given a CT volume V and a candidate location $c=[c_x, c_y, c_z]$, two additional image representations were considered for comparison: a standard image representation and a 2.5D approach. In the following discussion, these two image representations are explained.

Standard Image Representation

The standard image representation consists of extracting three crops from the conventional planes (sagittal, coronal, and axial planes):

$$I_{axial} = V(c_x-i, c_y-j, c_z)$$

$$I_{sagittal} = V(c_x, c_y-j, c_z-k)$$

$$I_{coronal} = V(c_x-i, c_y, c_z-k)$$

that are further stacked to form an rgb-like image. Data augmentation is performed by moving c along a random direction, by rotating the axial plane around the z-axis by a random degree, and by interpolating the three standard planes at different resolutions.

2.5D Image Representation

The 2.5D image representation begins with extracting a sub-volume $V_c$ around the candidate location, followed by rotating it around a randomly oriented vector, resulting in a rotated sub-volume, $$V\frac{rot}{\varepsilon}.$$

Next, three crops are extracted from the new sagittal, coronal, and axial planes, $$I_{axial} = V\frac{rot}{c}(c_x - i, c_y - j, c_z)$$

$$I_{sagittal} = V\frac{rot}{c}(c_x, c_y - j, c_z - k)$$

$$I_{coronal} = V\frac{rot}{c}(c_x - i, c_y, c_z - k)$$

and then stacked to form an rgb-like image. For orientation-based data augmentation, one can choose several rotation angles at random. For translation-based data augmentation, one can move the center of the subvolume along a random direction. Scaling can also be implemented by interpolating the new planes at different resolutions.

Discussion

In the description above regarding overall performance evaluation, it was demonstrated that embodiments of the invention (VOIR) have the highest overall performance across various architectures. One could also observe that, while the shallower models trained using standard and 2.5D image representations perform undesirably, VOIR can compensate for the inadequate depth of such architectures, enabling shallower models to yield significantly higher performance levels. It is also noteworthy that the standard image representation typically outperformed the 2.5D approach, probably because PE candidates have appeared more often in the vessels that are parallel to conventional imaging planes and thus standard image representation, which uses sagittal, coronal, and axial views, can capture a relatively more consistent representation of an embolus than the 2.5D approach.

In FIGS. 13A and 13B, it was shown that using deeper architectures improved PE detection performance. In particular, significant performance gains were observed after switching to the deep architectures fine-tuned from the ImageNet model. Yet, within the deep models, one can see that GoogleNet, which has the largest number of layers, is a strong winner across the three image representations. This superiority may suggest that deploying deeper models such as ResNet and DenseNet could further improve performance. Note that the goal of the experimentation was not to achieve the highest-performing PE detection system, nor a superficial comparison between architectures of varying depths; rather, the purpose was to systematically evaluate the impact of the imaging representation according to embodiments of the invention against two popular, widely-used image representations, namely the standard and the 2.5D approaches.

FIG. 14 shows that the handcrafted approach discussed above outperforms shallow architectures (sh-CNN, LeNet, and rd-CNN), if the latter are trained using standard and 2.5D image representations. While this superiority demonstrates the competence of the handcrafted approach, it also indicates that the convolutional networks do not meet expectations if they are not trained with the proper image representation. In fact, it is only after using embodiments of the invention (VOIR) that shallower models outperform the handcrafted approach. Therefore, designing the optimal image representation is a critical factor when training a high-performing classification model.

In the discussion above regarding the size of the training set, it was shown that embodiments of the invention (VOIR) achieve the greatest robustness against the size of the training set. It is also interesting to note that, with VOIR, one can achieve a similar level of performance using a substantially smaller training set. For instance, the GoogleNet model trained using VOIR with 25% of the training set outperforms the GoogleNet models that are trained using other image representations with 50% of the training data. For VGG and AlexNet, it is a draw; that is, performance of VGG and AlexNet models trained using VOIR and 50% of the training data is comparable to these model when trained using other image representations with the full dataset. For shallower architectures, models trained using VOIR with 25% of the training data significantly outperform their counterparts trained using the full training set. These comparisons demonstrate how a suitable image representation compensates for limited training data.

FIGS. 15A and 15B show that the normalized pAUC for all architectures improves as the training set grows in size. While this observation is expected, the curves show no evidence of performance plateau. In particular, the large increase in normalized pAUC for rd-CNN, GoogleNet, and AlexNet when their training set is changed from 50% to 100% indicates that these models could perform even better with additional training data, suggesting that the size of our training set is probably not adequate for the data-hungry deep convolutional models. It is possible that a higher performing PE CAD system could be obtained using a larger training set.

It was demonstrated in FIG. 17 that GoogleNet trained with embodiments of the invention (VOIR) outperformed the 3D CNNs trained with a 3D representation. This superiority is attributed to the capabilities of embodiments of the invention in handling the challenge of dimensionality and small sample size. First, the embodiments mitigate the challenge of dimensionality by condensing the essence of the 3D context around a PE into a compact 2D representation, leaving an easier task for 2D models to solve. A 3D representation, on the other hand, exposes the 3D models to a high dimensional input space, which, in turn, complicates the process of representation learning. Second, the embodiments properly handle the small sample size issue by generating diverse augmented images. This is because each augmented image generated according to the embodiments is the result of projecting the 3D context into longitudinal and cross-sectional image planes, and, thus, the augmented images are loosely correlated, exhibiting substantial variations in foreground and background appearance. A 3D representation, on the other hand, is handicapped by the small sample size issue, because traditional data augmentation in 3D may not substantially increase the effective sample size as the augmented image cubes often resemble the appearance of the original image cubes. A higher level of performance for the 3D models may be possible through pre-training with self-supervised schemes.

CONCLUSION

Embodiments of the invention provide a novel vessel-oriented image representation (VOIR) that enhances visualization of suspected emboli detected by radiologists and emboli candidates identified by PE CAD systems. Various CNN architectures trained using VOIR can significantly outperform their counterparts trained using standard and 2.5D image representations. Experiments further showed that the models trained using VOIR were more robust against the size of training set, exhibiting less performance degradation when the training set is halved or quartered in size. Experiments also showed that architectures trained using VOIR would require substantially smaller training sets to achieve performance equivalent to other image representations. Convergence speed of the models trained using the three image representations was compared, and it was concluded that VOIR enables the fastest convergence for the architectures under study. Additionally, a PE CAD operating in accordance with embodiments of the invention were compared against a carefully designed handcrafted approach and demonstrated significant performance gains. The PE CAD system also outperformed the winning system from the PE challenge at 0 mm localization error.

Figure 18:
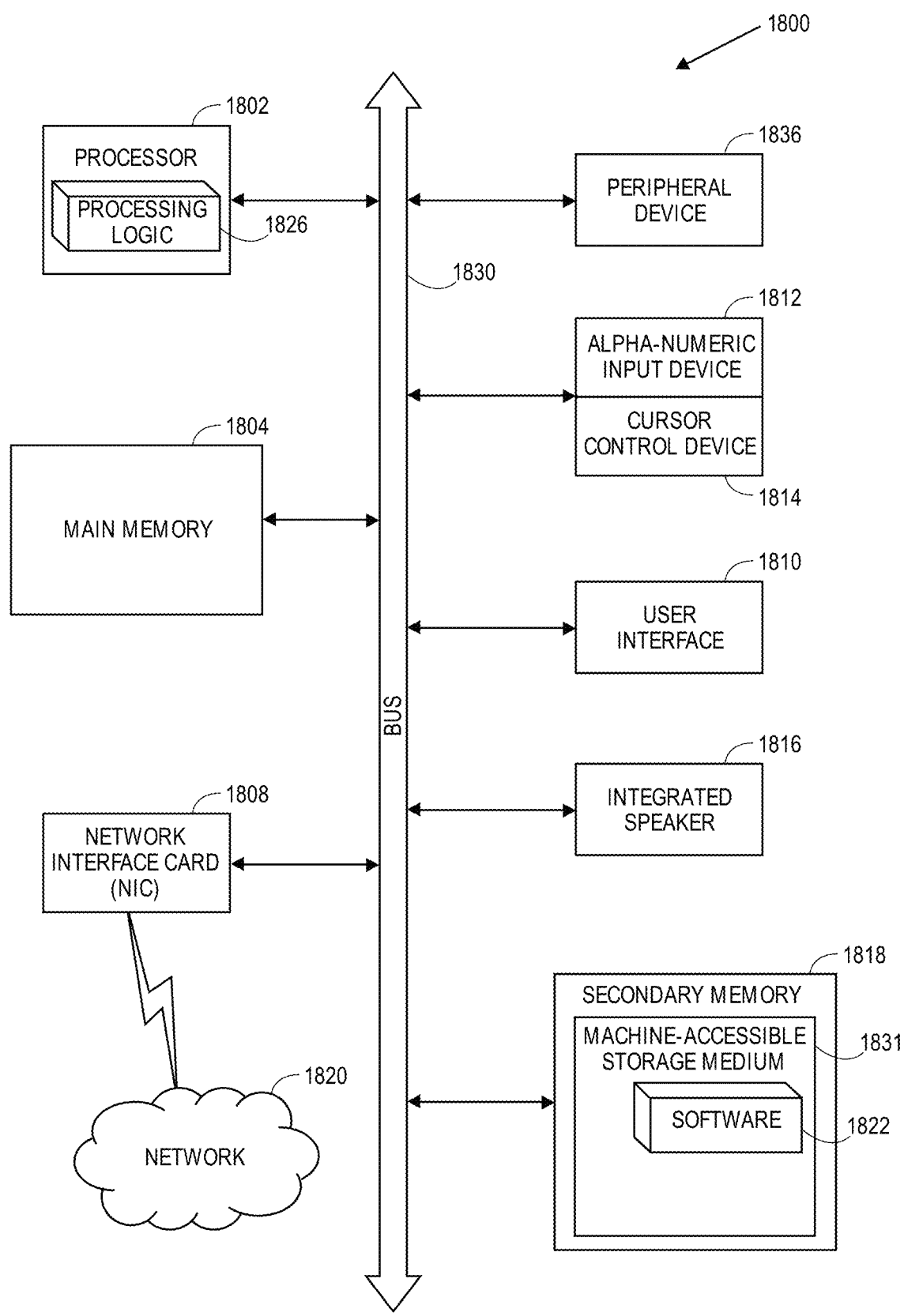
FIG. 18 illustrates a diagrammatic representation of a machine 1800 in the exemplary form of a computer system, in accordance with one embodiment, within which a set of instructions cause the machine 1800 to perform any one or more of the methodologies discussed herein.

FIG. 18 illustrates a diagrammatic representation of a machine 1800 in the exemplary form of a computer system, in accordance with one embodiment, within which a set of instructions, for causing the machine 1700 to perform any one or more of the methodologies discussed herein, may be executed. In alternative embodiments, the machine may be connected, networked, interfaced, etc., with other machines in a Local Area Network (LAN), a Wide Area Network, an intranet, an extranet, or the Internet. The machine may operate in the capacity of a server or a client machine in a client-server network environment, or as a peer machine in a peer to peer (or distributed) network environment. Certain embodiments of the machine may be in the form of a personal computer (PC), a tablet PC, a set-top box (STB), a Personal Digital Assistant (PDA), a cellular telephone, a web appliance, a server, a network router, switch or bridge, computing system, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein.

The exemplary computer system 1800 includes a processor 1802, a main memory 1804 (e.g., read-only memory (ROM), flash memory, dynamic random access memory (DRAM) such as synchronous DRAM (SDRAM) or Rambus DRAM (RDRAM), etc., static memory such as flash memory, static random access memory (SRAM), etc.), and a secondary memory 1818, which communicate with each other via a bus 1830. Main memory 1804 includes information and instructions and software program components necessary for performing and executing the functions with respect to the various embodiments of the systems, methods for implementing embodiments of the invention described herein. Instructions may be stored within main memory 1804. Main memory 1804 and its sub-elements are operable in conjunction with processing logic 1826 and/or software 1822 and processor 1802 to perform the methodologies discussed herein.

Processor 1802 represents one or more devices such as a microprocessor, central processing unit, or the like. More particularly, the processor 1802 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processor 1802 may also be one or more devices such as an application specific integrated circuit (ASIC), a field programmable gate array (FPGA), a digital signal processor (DSP), network processor, or the like. Processor 1802 is configured to execute the processing logic 1826 for performing the operations and functionality which are discussed herein.

The computer system 1800 may further include one or more network interface cards 1808 to interface with the computer system 1800 with one or more networks 1820. The computer system 1800 also may include a user interface 1810 (such as a video display unit, a liquid crystal display (LCD), or a cathode ray tube (CRT)), an alphanumeric input device 1812 (e.g., a keyboard), a cursor control device 1814 (e.g., a mouse), and a signal generation device 1816 (e.g., an integrated speaker). The computer system 1800 may further include peripheral device 1836 (e.g., wireless or wired communication devices, memory devices, storage devices, audio processing devices, video processing devices, etc.). The computer system 1800 may perform the functions of the embodiments as described herein.

The secondary memory 1818 may include a non-transitory machine-readable storage medium (or more specifically a non-transitory machine-accessible storage medium) 1821 on which is stored one or more sets of instructions (e.g., software 1822) embodying any one or more of the methodologies or functions described herein. Software 1822 may also reside, or alternatively reside within main memory 1804, and may further reside completely or at least partially within the processor 1802 during execution thereof by the computer system 1800, the main memory 1804 and the processor 1802 also constituting machine-readable storage media. The software 1822 may further be transmitted or received over a network 1820 via the network interface card 1808.

Some portions of this detailed description are presented in terms of algorithms and representations of operations on data within a computer memory. These algorithmic descriptions and representations are the means used by those skilled in the data processing arts to most effectively convey the substance of their work to others skilled in the art. An algorithm is here, and generally, conceived to be a sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, as apparent from this discussion, it is appreciated that throughout the description, discussions utilizing terms such as "processing" or "computing" or "calculating" or "determining" or "displaying" or the like, refer to the action and processes of a computer system or computing platform, or similar electronic computing device(s), that manipulates and transforms data represented as physical (electronic) quantities within the computer system's registers and memories into other data similarly represented as physical quantities within the computer system memories or registers or other such information storage, transmission or display devices.

In addition to various hardware components depicted in the figures and described herein, embodiments further include various operations which are described below. The operations described in accordance with such embodiments may be performed by hardware components or may be embodied in machine-executable instructions, which may be used to cause a purpose processor programmed with the instructions to perform the operations. Alternatively, the operations may be performed by a combination of hardware and software, including software instructions that perform the operations described herein via memory and one or more processors of a computing platform.

Embodiments of invention also relate to apparatuses for performing the operations herein. Some apparatuses may be specially constructed for the required purposes, or selectively activated or configured by a computer program stored in one or more computers. Such a computer program may be stored in a computer readable storage medium, such as, but not limited to, any type of disk including optical disks, CD-ROMs, DVD-ROMs, and magnetic-optical disks, read-only memories (ROMs), random access memories (RAMs), EPROMs, EEPROMs, NVRAMs, magnetic or optical cards, or any type of media suitable for storing electronic instructions, and each coupled to a computer system bus.

The algorithms presented herein are not inherently related to any particular computer or other apparatus. In addition, embodiments of the invention are not described with reference to any particular programming language. It will be appreciated that a variety of programming languages may be used to implement the embodiments of the invention as described herein.

A machine-readable medium includes any mechanism for storing or transmitting information in a form readable by a machine (e.g., a computer). For example, a machine-readable medium includes read only memory ("ROM"); random access memory ("RAM"); magnetic disk storage media; optical storage media; flash memory devices, etc.

Although the invention has been described and illustrated in the foregoing illustrative embodiments, it is understood that the present disclosure has been made only by way of example, and that numerous changes in the details of implementation of the invention can be made without departing from the spirit and scope of the invention, which is only limited by the claims that follow. Features of the disclosed embodiments can be combined and rearranged in various ways.

What is claimed is:

1. A method of detecting a pulmonary embolism (PE) in an image dataset of a blood vessel, comprising:
    obtaining a volume of interest (VOI) within the blood vessel;
    generating a plurality of PE candidates within the VOI;
    generating a set of voxels for each of the plurality of PE candidates within the VOI;
    estimating for each PE candidate a longitudinal axis of the blood vessel that contains the PE candidate, given the set of voxels for the PE candidates;
    generating a first imaging plane envelope that contains a plurality of cross sectional image planes and a second imaging plane envelope that contains a plurality of longitudinal image planes, each of the plurality of cross sectional and longitudinal image planes successively rotated around the estimated longitudinal axis of the blood vessel that contains the PE candidate;
    generating a three-channel representation of the blood vessel that contains the PE candidate by:
        selecting randomly one of the plurality of cross sectional image planes from the first imaging plane envelope;

selecting randomly two of the plurality of longitudinal image planes from the second imaging plane envelope; and receiving user input selecting a PE candidate location in the three-channel representation of the blood vessel that contains the PE candidate;

displaying the selected PE candidate location in the three-channel representation of the blood vessel that contains the PE candidate in which the longitudinal axis of the blood vessel substantially aligns with a vertical centerline of a two-dimensional display device;

animating, in a plurality of frames, the display of the selected PE candidate location in the three-channel representation of the blood vessel that contains the PE candidate while the longitudinal axis of the blood vessel continues to substantially align with the vertical centerline of the two-dimensional display device, wherein each of the plurality of frames is constructed by interpolating the VOI within the blood vessel along the longitudinal axis of the blood vessel and at an angle of rotation around the longitudinal axis of the blood vessel.

2. The method of claim 1, wherein estimating for each PE candidate the longitudinal axis of the blood vessel that contains the PE candidate comprises:

obtaining a subvolume for the PE candidate; erasing a filling defect at a location of the PE candidate;

identifying a set of voxels that represent the blood vessel that contains the PE candidate; and estimating the longitudinal axis of the vessel based on the identified set of voxels that represent the blood vessel that contains the PE candidate.

3. The method of claim 2, wherein erasing a filling defect at a location of the PE candidate comprises replacing voxel intensities within a portion of the set of voxels that comprise the PE candidate with a constant blood vessel-like intensity.

4. The method of claim 2, wherein identifying the set of voxels that represent the blood vessel that contains the PE candidate comprises:

analyzing a plurality of connected components in the subvolume for the PE candidate; and choosing a largest connected component from among the plurality of connected components in the subvolume for the PE candidate.

5. The method of claim 4, wherein analyzing the plurality of connected components in the subvolume for the PE candidate comprises:

scanning a portion of the set of voxels that comprise the subvolume;

grouping voxels in the portion of the set of voxels that comprise the subvolume into one of the plurality of connected components based on voxel connectivity; and labeling each voxel in the portion of the set of voxels that comprise the subvolume according to the one of the plurality of connected components in which it is grouped.

6. The method of claim 4, wherein estimating the longitudinal axis of the blood vessel based on the identified set of voxels that represent the blood vessel that contains the PE candidate comprises performing principal component analysis on a matrix of coordinates of a portion of the set of voxels that comprise the largest connected component.

7. A CAD system for detecting a pulmonary embolism (PE) in an image dataset of a blood vessel, the system comprising;

a processor;
a memory; and
CAD system logic to cause the CAD system to perform operations including:

obtaining a volume of interest (VOI) within the blood vessel;

generating a plurality of PE candidates within the VOI;

generating a set of voxels for each of the plurality of PE candidates within the VOI; and estimating for each PE candidate a longitudinal axis of the blood vessel that contains the PE candidate, given the set of voxels for the PE candidate; and generating a first imaging plane envelope that contains a plurality of cross sectional image planes and a second imaging plane envelope that contains a plurality of longitudinal image planes, each of the plurality of cross sectional and longitudinal image planes successively rotated around the estimated longitudinal axis of the blood vessel that contains the PE candidate;

generating a three-channel representation of the blood vessel that contains the PE candidate by:

selecting randomly one of the plurality of cross sectional image planes from the first imaging plane envelope;

selecting randomly two of the plurality of longitudinal image planes from the second imaging plane envelope; and receiving user input selecting a PE candidate location in the three-channel representation of the blood vessel that contains the PE candidate;

displaying the selected PE candidate location in the three-channel representation of the blood vessel that contains the PE candidate in which the longitudinal axis of the blood vessel substantially aligns with a vertical centerline of a two-dimensional display device;

animating, in a plurality of frames, the display of the selected PE candidate location in the three-channel representation of the blood vessel that contains the PE candidate while the longitudinal axis of the blood vessel continues to substantially align with the vertical centerline of the two-dimensional display device, wherein each of the plurality of frames is constructed by interpolating the VOI within the blood vessel along the longitudinal axis of the blood vessel and at an angle of rotation around the longitudinal axis of the blood vessel.

8. The CAD system of claim 7, wherein estimating for each PE candidate the orientation of the blood vessel that contains the PE candidate comprises:

obtaining a subvolume for the PE candidate;
erasing a filling defect at a location of the PE candidate;
identifying a set of voxels that represent the blood vessel that contains the PE candidate; and
estimating the longitudinal axis of the blood vessel based on the identified set of voxels that represent the blood vessel that contains the PE candidate.

9. The CAD system of claim 8, wherein erasing a filling defect at a location of the PE candidate comprises replacing voxel intensities within a portion of the set of voxels that comprise the PE candidate with a constant blood vessel-like intensity.

10. The CAD system of claim 8, wherein identifying the set of voxels that represent the blood vessel that contains the PE candidate comprises:

analyzing a plurality of connected components in the subvolume for the PE candidate; and choosing a largest connected component from among the plurality of connected components in the subvolume for the PE candidate.

11. The CAD system of claim 10, wherein analyzing the plurality of connected components in the subvolume for the PE candidate comprises:
scanning a portion of the set of voxels that comprise the subvolume;
grouping voxels in the portion of the set of voxels that comprise the subvolume into one of the plurality of connected components based on voxel connectivity; and
labeling each voxel in the portion of the set of voxels that comprise the subvolume according to the one of the plurality of connected components in which it is grouped.

12. The CAD system of claim 10, wherein estimating the longitudinal axis of the blood vessel based on the identified set of voxels that represent the blood vessel that contains the PE candidate comprises performing principal component analysis on a matrix of coordinates of a portion of the set of voxels that comprise the largest connected component.

13. Non-transitory computer readable storage media having instructions stored thereon that, when executed by a processor of a CAD system, the instructions cause the CAD system to detect a pulmonary embolism (PE) in an image dataset of a blood vessel by performing operations including:
obtaining a volume of interest (VOI) within the blood vessel;
generating a plurality of PE candidates within the VOI;
generating a set of voxels for each of the plurality of PE candidates within the VOI; and
estimating for each PE candidate a longitudinal axis of the blood vessel that contains the PE candidate, given the set of voxels for the PE candidate; and
generating a first imaging plane envelope that contains a plurality of cross sectional image planes and a second imaging plane envelope that contains a plurality of longitudinal image planes, each of the plurality of cross sectional and longitudinal image planes successively rotated around the estimated longitudinal axis of the blood vessel that contains the PE candidate;
generating a three-channel representation of the blood vessel that contains the PE candidate by:
selecting randomly one of the plurality of cross sectional image planes from the first imaging plane envelope;
selecting randomly two of the plurality of longitudinal image planes from the second imaging plane envelope; and
receiving user input selecting a PE candidate location in the three-channel representation of the blood vessel that contains the PE candidate;
displaying the selected PE candidate location in the three-channel representation of the blood vessel that contains the PE candidate in which the longitudinal axis of the blood vessel substantially aligns with a vertical centerline of a two-dimensional display device;
animating, in a plurality of frames, the display of the selected PE candidate location in the three-channel representation of the blood vessel that contains the PE candidate while the longitudinal axis of the blood vessel continues to substantially align with the vertical centerline of the two-dimensional display device, wherein each of the plurality of frames is constructed by interpolating the VOI within the blood vessel along the longitudinal axis of the blood vessel and at an angle of rotation around the longitudinal axis of the blood vessel.

14. The non-transitory computer readable storage media of claim 13, wherein estimating for each PE candidate the longitudinal axis of the blood vessel that contains the PE candidate comprises:
obtaining a subvolume for the PE candidate;
erasing a filling defect at a location of the PE candidate;
identifying a set of voxels that represent the blood vessel that contains the PE candidate; and
estimating the longitudinal axis of the blood vessel based on the identified set of voxels that represent the blood vessel that contains the PE candidate.

* * * * *